(12) United States Patent
Allred et al.

(10) Patent No.: US 6,981,874 B2
(45) Date of Patent: *Jan. 3, 2006

(54) DENTAL BLEACHING COMPOSITIONS AND DEVICES HAVING A SOLID ACTIVATION ADHESIVE LAYER OR REGION AND BLEACHING GEL LAYER OR REGION

(75) Inventors: Peter M. Allred, Riverton, UT (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/784,063

(22) Filed: Feb. 19, 2004

(65) Prior Publication Data

US 2005/0089821 A1    Apr. 28, 2005

Related U.S. Application Data

(63) Continuation-in-part of application No. 10/728,525, filed on Dec. 5, 2003, which is a continuation-in-part of application No. 10/692,117, filed on Oct. 22, 2003.

(51) Int. Cl.
*A61C 5/00* (2006.01)
*A61C 17/02* (2006.01)

(52) U.S. Cl. .................................. 433/215; 433/80
(58) Field of Classification Search ............. 433/80, 433/215, 216; 424/53; 206/63.5, 369
See application file for complete search history.

(56) References Cited

U.S. PATENT DOCUMENTS

| | | |
|---|---|---|
| 2,835,628 A | 5/1958 | Saffir .......................... 167/84 |
| 3,688,406 A | 9/1972 | Porter et al. ................. 32/40 R |
| RE33,093 E | 10/1989 | Schiraldi et al. ............. 424/676 |
| 4,900,721 A | 2/1990 | Bansemir |
| 5,008,093 A | 4/1991 | Merianos |
| 5,108,742 A | 4/1992 | Merianos |
| 5,112,225 A | 5/1992 | Diesso ......................... 433/48 |
| 5,183,901 A | 2/1993 | Login et al. |
| 5,310,563 A | 5/1994 | Curtis et al. ................. 424/616 |
| 5,326,685 A | 7/1994 | Gaglio et al. ................ 433/215 |
| 5,346,061 A | 9/1994 | Newman et al. ............. 206/221 |
| 5,425,953 A | 6/1995 | Sintov et al. ................ 424/404 |
| 5,562,449 A | 10/1996 | Jacobs et al. ................ 433/215 |

(Continued)

OTHER PUBLICATIONS

Technical Bulletin: Hydrogen Peroxide-Polyvinylpyrrolidone Poylmer Complexes, International Specialty Products, 1361 Alps Road, Wayne New Jersey 07470, www.ispcorp.com (Dec. 2003).

*Primary Examiner*—Cary E. O'Connor
(74) *Attorney, Agent, or Firm*—Workman Nydegger

(57) ABSTRACT

Dental bleaching compositions in the shape of a dental tray, strip or patch include an adhesive activation composition and a dental bleaching gel. A barrier layer may be included to form a dental bleaching device that protects the bleaching composition from saliva or moisture during use. The adhesive activation composition is substantially solid and has increased adhesiveness to oral tissue when moistened with saliva or water. The adhesive activation composition is formed from an intermediate composition that is heated to drive off the solvent. Using a bleaching gel separate from the adhesive activation composition improves the potency and stability of the bleaching agent prior to use. During use, saliva or moisture cause the bleaching gel to be activated as the bleaching agent activator in the activation composition is leached therefrom so as to react with and destabilize the bleaching agent within the bleaching gel.

51 Claims, 11 Drawing Sheets

U.S. PATENT DOCUMENTS

| | | | |
|---|---|---|---|
| 5,575,654 A | 11/1996 | Fontenot | 433/215 |
| 5,611,687 A | 3/1997 | Wagner | 433/80 |
| 5,616,027 A | 4/1997 | Jacobs et al. | 433/37 |
| 5,639,445 A | 6/1997 | Curtis et al. | 424/49 |
| 5,707,235 A | 1/1998 | Knutson | 433/213 |
| 5,711,935 A | 1/1998 | Hill et al. | 424/49 |
| 5,752,826 A * | 5/1998 | Andreiko | 433/41 |
| 5,769,633 A | 6/1998 | Jacobs et al. | 433/37 |
| 5,816,802 A | 10/1998 | Montgomery | 433/80 |
| 5,846,058 A | 12/1998 | Fischer | 433/216 |
| 5,863,202 A | 1/1999 | Fontenot et al. | 433/215 |
| 5,879,691 A | 3/1999 | Sagel et al. | 429/401 |
| 5,891,453 A | 4/1999 | Sagel et al. | 424/401 |
| 5,894,017 A | 4/1999 | Sagel et al. | 424/401 |
| 5,922,307 A | 7/1999 | Montgomery | 424/53 |
| 5,924,863 A | 7/1999 | Jacobs et al. | 433/80 |
| 5,980,249 A | 11/1999 | Fontenot | 433/80 |
| 5,989,569 A | 11/1999 | Dirksing et al. | 424/401 |
| 6,045,811 A | 4/2000 | Dirksing et al. | 424/401 |
| 6,080,397 A | 6/2000 | Pfirrmann | |
| 6,089,869 A * | 7/2000 | Schwartz | 433/215 |
| 6,096,328 A | 8/2000 | Sagel et al. | 424/401 |
| 6,106,293 A | 8/2000 | Wiesel | 433/215 |
| 6,126,443 A | 10/2000 | Burgio | 433/215 |
| 6,136,297 A | 10/2000 | Sagel et al. | 424/49 |
| 6,142,780 A | 11/2000 | Burgio | 433/80 |
| 6,155,832 A | 12/2000 | Wiesel | 433/215 |
| 6,183,251 B1 | 2/2001 | Fischer | 433/48 |
| 6,197,331 B1 | 3/2001 | Lerner et al. | 424/448 |
| 6,247,930 B1 | 6/2001 | Chiang et al. | 433/80 |
| 6,274,122 B1 | 8/2001 | McLaughlin | 424/53 |
| 6,277,458 B1 | 8/2001 | Dirksing et al. | 424/42.3 |
| 6,280,196 B1 | 8/2001 | Berghash | 433/215 |
| 6,287,120 B1 | 9/2001 | Wiesel | 433/215 |
| 6,322,360 B1 | 11/2001 | Burgio | 433/80 |
| 6,331,292 B1 | 12/2001 | Montgomery | 424/53 |
| 6,343,932 B1 | 2/2002 | Wiesel | 433/215 |
| 6,419,903 B1 | 7/2002 | Xu et al. | 424/49 |
| 6,419,906 B1 | 7/2002 | Xu et al. | 424/53 |
| 6,435,873 B1 | 8/2002 | Burgio | 433/80 |
| 6,440,396 B1 | 8/2002 | McLaughlin | 424/49 |
| 6,458,380 B1 | 10/2002 | Leaderman | 424/443 |
| 6,461,158 B1 | 10/2002 | Sagel et al. | 433/30 |
| 6,488,914 B2 | 12/2002 | Montgomery | 424/53 |
| 6,497,575 B2 | 12/2002 | Zavitsanos et al. | 433/215 |
| 6,500,408 B2 | 12/2002 | Chen | 424/53 |
| 6,503,486 B2 | 1/2003 | Xu et al. | 424/53 |
| 6,506,053 B2 | 1/2003 | Wiesel | 433/215 |
| 6,514,483 B2 | 2/2003 | Xu et al. | 424/53 |
| 6,514,484 B2 | 2/2003 | Rajaiah et al. | 424/53 |
| 6,551,579 B2 | 4/2003 | Sagel et al. | 424/53 |
| 6,649,147 B2 | 11/2003 | Ye et al. | 424/49 |
| 6,682,721 B2 | 1/2004 | Kim et al. | 424/53 |
| 6,689,344 B2 | 2/2004 | Chang et al. | |
| 6,730,316 B2 | 5/2004 | Chen | |
| 2001/0046654 A1 | 11/2001 | Zavitsanos et al. | 433/32 |
| 2002/0006387 A1 | 1/2002 | Sagel et al. | 424/53 |
| 2002/0006388 A1 | 1/2002 | Sagel et al. | 424/53 |
| 2002/0012685 A1 | 1/2002 | Sagel et al. | 424/401 |
| 2002/0018754 A1 | 2/2002 | Sagel et al. | 424/49 |
| 2002/0081555 A1 | 6/2002 | Wiesel | 433/215 |
| 2002/0164292 A1 | 11/2002 | Peterson et al. | 424/53 |
| 2002/0182154 A1 | 12/2002 | McLaughlin | 424/53 |
| 2002/0187111 A1 | 12/2002 | Xu et al. | 424/53 |
| 2002/0187112 A1 | 12/2002 | Xu et al. | 424/53 |
| 2003/0003421 A1 | 1/2003 | Besenheider et al. | 433/215 |
| 2003/0012747 A1 | 1/2003 | Peterson | 424/53 |
| 2003/0036037 A1 | 2/2003 | Zavitsanos et al. | 433/215 |
| 2003/0044631 A1 | 3/2003 | Sagal et al. | 428/548 |
| 2003/0068284 A1 | 4/2003 | Sagel et al. | 424/53 |
| 2003/0068601 A1 | 4/2003 | Zavitsanos et al. | 433/215 |
| 2003/0082114 A1 | 5/2003 | Kim et al. | 424/53 |
| 2003/0133884 A1 | 7/2003 | Chang et al. | 424/53 |
| 2003/0194382 A1 | 10/2003 | Chang et al. | 424/53 |
| 2003/0198606 A1 | 10/2003 | Kim et al. | 424/53 |

* cited by examiner

DENTAL BLEACHING COMPOSITIONS AND DEVICES HAVING A SOLID ACTIVATION ADHESIVE LAYER OR REGION AND BLEACHING GEL LAYER OR REGION

CROSS-REFERENCE TO RELATED APPLICATIONS

This application is a continuation-in-part of U.S. application Ser. No. 10/728,525, filed Dec. 5, 2003, which is a continuation-in-part of U.S. application Ser. No. 10/692,117, filed Oct. 22, 2003. The foregoing applications are incorporated herein in their entirety.

BACKGROUND OF THE INVENTION

1. The Field of the Invention

This invention is in the field of dental bleaching compositions and devices used to bleach a person's teeth. More particularly, the invention relates to bleaching compositions and devices that include a substantially solid adhesive composition containing a bleaching agent activator, a dental bleaching gel, and optionally a moisture-resistant barrier layer.

2. The Relevant Technology

Virtually all people desire white or whiter teeth. To achieve this goal, people either have veneers placed over their teeth or have their teeth chemically bleached. In the past, patients who desired to have their teeth bleached had to submit to conventional in-office bleaching techniques. The process generally involves: (1) making an alginate impression of the patient's teeth; (2) making a stone cast or model of the impression; (3) vacuum forming a dental tray from the model, usually from a heated sheet of thin ethyl vinyl acetate (EVA) material, and (4) trimming to exclude gingival coverage. This method results in a tray that is soft and flexible, that is customized to very accurately fit over the patient's teeth, and that is therefore very comfortable to wear. However, the process for making a customized tray is time consuming, often taking days or weeks before the customized tray is available to the patient, and the resulting tray can be expensive.

Because of the time and cost associated with making customized trays, less time consuming and costly alternatives have been developed. Contrary to marketing campaigns, however, many alternatives have substantial disadvantages, primarily in terms of their effectiveness (or lack thereof) in actually bleaching teeth. They also have their own unique issues relating to difficulty of use, low comfort, and poor taste (bleaching and other oral treatment compositions are, after all, placed directly into a person's mouth).

One alternative to customized dental trays are non-customized trays that approximate the shapes and sizes of a variety of users' dental arches. While non-customized dental trays can be used without the need for a professional customization procedure by a dentist, such trays tend to be more bulky and less comfortable than custom-fitted trays. Dental trays that can be self-customized (e.g., so-called "boil-and-bite" trays) are somewhat more comfortable and better-fitting compared to non-custom trays but less comfortable than trays that are customized by a dentist.

Another alternative tooth bleaching method involves painting a bleaching composition directly onto the surfaces of a person's teeth to be bleached. An advantage of this procedure is that it eliminates the need to obtain a customized tray, or even a non-custom tray. The main disadvantage, however, is that the bleaching composition remains directly exposed to the person's saliva and disruptive forces and movements normally found within a person's mouth. The result is that a significant portion of the bleaching composition does not remain on the tooth where bleaching is desired. Instead, some or all of the composition can dissolve away into the person's saliva and/or be transferred to adjacent oral tissues. Because paint-on dental bleaching compositions, like all dental bleaching compositions, contain peroxide-based bleaching agents, irritation to soft oral tissues within the user's mouth and throat is a potential problem when using such compositions.

Yet another alternative tooth bleaching method involves placing a flexible bleaching strip over a user's tooth surfaces. Bleaching strips typically comprise a flexible plastic strip coated with a moist dental bleaching gel of moderate viscosity and relatively low stickiness on the side of the strip facing the user's teeth. To install the bleaching strip, a portion of the bleaching strip is first placed over the front surfaces of the user's teeth, followed by folding the remainder of the strip around the occlusal edges of the teeth and back against a portion of the lingual surfaces. Like paint-on bleaching compositions, this procedure does not require the user to obtain a customized tray, or even a non-custom tray, into which a bleaching composition must be placed by the user prior to use. An advantage of bleaching strips over paint-on bleaching compositions is that bleaching strips include a barrier that, at least in theory, protects the dental bleaching gel from diffusing into the user's mouth.

In reality, however, because of the generally poor adhesion of bleaching strips to the user's teeth, coupled with their generally flimsy nature, it is often difficult for the user to maintain the bleaching strips in their proper position for the recommended time. Conventional bleaching strips are prone to slip off the teeth as a result of even minimal movement of the user's mouth, jaw or tongue. Indeed, it is recommended that the user not eat, drink, smoke or sleep while wearing the bleaching strip. In practice, it is difficult to talk and maintain the bleaching strips properly oriented over the teeth to be bleached.

Even if a user successfully maintains a conventional bleaching strip in its proper position during the recommended bleaching period, the bleaching often diffuses into the person's saliva, potentially causing a poor taste in the user's mouth and possibly discomfort to soft oral and throat tissues. The tendency of the bleaching gel to diffuse into the user's mouth can be accelerated through even minimal shifts of the bleaching strip over the user's teeth, with each shift potentially causing bleaching gel that remains adhered to the user's teeth, but not covered by the plastic strip, to be exposed to saliva in the user's mouth. In some cases, the bleaching strip can become so dislodged or mangled that it must be removed by the user and replaced with a fresh bleaching strip to complete the recommended bleaching time. This multiplies the cost and hassle of using conventional bleaching strips.

In practical terms, the use of conventional bleaching strips can greatly inhibit even the simplest of activities that involve movement of the user's mouth or tongue, such as talking, smiling, making other facial expressions, or even swallowing (which normally occurs subconsciously throughout the day). Indeed, the time when a person's mouth and tongue are the least prone to move is at night while the person is sleeping. Unfortunately, it is recommended that conventional bleaching strips not be used while sleeping, presumably to prevent accidental choking on an inadvertently dislodged bleaching strip. This only confirms the tendency of conventional bleaching strips to easily dislodge from a user's teeth.

Ultimately, the main impediment to successful bleaching is the failure of users to complete the prescribed bleaching regimen. If the bleaching apparatus is difficult to use, requires numerous repetitions to achieve observable results, or is simply uncomfortable or a hassle to wear, the user may simply give up and abort the bleaching process altogether. Thus, even if significant dental bleaching is possible using a particular bleaching product, it is less likely to occur where the inadequacies of the bleaching apparatus or method causes a user to become discouraged before desired results are attained.

In view of the foregoing, there is an ongoing need for improved bleaching apparatus and methods that are simple and easy to use, that reliably remain in position over the user's teeth so as to reduce diffusion of bleaching composition into a user's oral cavity. Such improvements would be expected to improve or encourage compliance by the user.

BRIEF SUMMARY OF THE PREFERRED EMBODIMENTS

The present invention generally relates to improved dental bleaching compositions and devices used to bleach a person's teeth. Dental bleaching compositions according to the invention include an adhesive layer comprising a substantially solid adhesive composition in the form of a dental tray, strip, patch or other desired shape that becomes more adhesive to teeth when moistened (e.g., by saliva or water), and a dental bleaching gel adjacent to the adhesive composition layer. Moistening the adhesive layer also causes it to release a bleaching agent activator that accelerates tooth bleaching by the dental bleaching gel. The dental bleaching gel may comprise a bead, a continuous layer, or a plurality of discontinuous regions or islands.

Dental bleaching devices according to the invention include a moisture-resistant barrier layer, such as a dental tray, strip, or patch, or a thin membrane having no predefined shape, an adhesive composition comprising a substantially solid adhesive composition that becomes more adhesive to teeth when moistened (e.g., by saliva or water) adjacent to the barrier layer, and a dental bleaching gel adjacent to at least one of the adhesive or barrier layer. Moistening the adhesive composition also causes it to release a bleaching agent activator that accelerates tooth bleaching by the dental bleaching gel. The dental bleaching gel may comprise a bead, a continuous layer, or a plurality of discontinuous regions or islands. In the case where the barrier layer is a dental tray, strip or patch, the adhesive layer may be a continuous layer or a plurality of discontinuous regions. In the case where the barrier layer comprises a thin membrane having no predefined shape, the adhesive layer is advantageously shaped like a dental tray, strip or patch to give the bleaching device form. To the extent that a barrier layer is subsequently applied or attached to an existing dental bleaching composition comprising (i) an adhesive layer and (ii) bleaching gel, the bleaching composition may be considered to be an intermediate to the finished dental bleaching device comprising the bleaching composition and the barrier layer.

The optional barrier layer advantageously comprises a thin, flexible membrane formed from a moisture-resistant polymer material. Nevertheless, it is within the scope of the invention to provide barrier layers having any desired thickness or rigidity. In a preferred embodiment, the barrier layer comprises a thin layer of a polyolefin, polyester, EVA, polyurethane, or similar moisture-resistant material. The barrier layer may comprise a conventional dental tray, examples of which include both customized and non-custom dental trays, or it may comprise a substantially flat strip or patch. The barrier layer may be as simple as a layer of a moisture resistant barrier-forming material that is sprayed or painted on, applied by dipping, or otherwise applied to an existing adhesive layer comprising a substantially solid adhesive composition (e.g., one that is in the form of a dental tray, strip or patch).

The substantially solid adhesive composition comprises at least one tooth adhesion agent that contributes or provides increased adhesiveness to teeth when moistened by saliva or water, at least one bleaching agent activator, and optionally at least one active agent. When placed over a person's teeth, the adhesive composition reliably adheres to the teeth, thereby maintaining reliable contact between the dental bleaching gel and a person's teeth to be bleached. The moistened adhesive composition or layer also releases the bleaching agent activator, which then reacts with and destabilizes the bleaching agent within the bleaching gel. A barrier layer is advantageously provided to protect the adhesive composition and bleaching gel from diffusing away from the person's teeth into the oral cavity as a result of ambient saliva or moisture found within the person's mouth.

In one embodiment, the adhesive composition advantageously comprises one or more coherent regions or masses that do not readily run or flow, as opposed to a liquid, gel, or dry particulate or powdery composition. A substantially solid and coherent adhesive composition in combination with a gel better adheres to a person's teeth and does not readily diffuse into the surrounding oral cavity on its own, absent becoming diluted by saliva or moisture in a person's mouth, compared to a gel used by itself. This helps maintain the adhesive composition and bleaching gel between the barrier layer and a person's teeth being bleached and helps prevent diffusion of the bleaching agent into the surrounding oral cavity. This, in turn, promotes better tooth bleaching, patient compliance, and reduces the tendency of the user to taste the bleaching composition when in use.

The tooth adhesion agent within the adhesive composition contributes or provides increased adhesiveness to teeth when moistened with saliva or water. In one embodiment, the tooth adhesion agent advantageously remains substantially non-adhesive when the adhesive composition is in a dry or substantially solid condition but becomes adhesive to teeth when the adhesive composition is moistened with, e.g., water or saliva. A non-limiting example of a suitable tooth adhesion agent is polyvinyl pyrrolidone (PVP), although it is within the scope of the invention to use other tooth adhesion agents known in the art.

The adhesive composition, as well as intermediate compositions used to make the substantially solid adhesive composition, may include other components as desired to yield a final composition having desired properties. These include both inert components and active agents. Examples of inert components include, but are not limited to, plasticizers and humectants (e.g., glycerin, sorbitol, and polyethylene glycol), volatile solvents (e.g., water and alcohols), neutralizing agents, thickening agents (e.g., fumed silica), flavorants, sweeteners, and the like.

Examples of active agents (in addition to the bleaching agent activator) include desensitizing agents (e.g., potassium nitrate), remineralizing agents (e.g., sodium fluoride or other fluoride salts), antimicrobial agents (e.g., chlorhexidine), antiplaque agents, anti-tartar agents, or other medicaments.

Examples of useful bleaching agent activators include bases (e.g., sodium hydroxide, potassium hydroxide, sodium bicarbonate and amines), metals or metal ion compounds (e.g., iron, zinc, and manganese metals or compounds), an enzymes (e.g., catalase).

In one embodiment, the dental bleaching gel comprises a dental bleaching agent and a tackifying agent, typically dispersed within a liquid carrier or vehicle. Exemplary dental bleaching agents include aqueous hydrogen peroxide, carbamide peroxide, sodium perborate, sodium percarbonate, and the like. It is, of course, within the scope of the invention to use any dental bleaching agent known in the art.

Exemplary tackifying agents include PVP, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like. It is, of course, within the scope of the invention to use any tackifying agent known in the art.

Exemplary liquid carriers or vehicles include water, alcohols, polyols (e.g., glycerin, sorbitol, polyethylene glycol, propylene glycol, and polypropylene glycol), and the like.

According to one embodiment, the substantially solid adhesive composition is made by first forming a flowable liquid or gel composition intermediate that is subsequently dried to form a substantially solid adhesive composition. This may be performed by heating or otherwise causing one or more volatile solvents to be driven off by evaporation, thus leaving behind the substantially solid composition or layer. The drying process may be performed before or after the adhesive activation composition intermediate is placed into contact with a barrier layer. In one embodiment, the intermediate composition is cast onto a forming surface, dried and removed to yield a substantially solid sheet that is cut, stamped or otherwise formed into a desired shape (e.g., tray, strip or patch). Thereafter, a bleaching gel is attached or applied to an inner surface of the adhesive activation composition and a barrier layer is optionally applied or attached to an outer surface of the adhesive activation composition. The bleaching gel can be applied to the adhesive activation composition before or after the barrier layer, or in the absence of a barrier layer. At least a portion of bleaching gel can be applied directly adjacent to the barrier layer.

One advantage of providing a bleaching gel separate from the adhesive activation composition is that the adhesive composition contains a bleaching agent activator that diffuses or leaches out of the adhesive layer and activates the bleaching gel upon moistening at least one of the bleaching gel or adhesive layer with saliva or water. The result is accelerated bleaching. According to one embodiment, the bleaching gel is initially substantially anhydrous and/or does not initially contact the adhesive composition in order to minimize diffusion or leaching of the bleaching agent activator out of the adhesive activation layer and into the bleaching gel prior to use.

Another advantage of providing a bleaching gel that is separate from the adhesive layer, rather than a bleaching agent that is contained within the adhesive layer, is that it provides a bleaching composition or device that is more stable or consistent relative to the amount of active bleaching agent. Heating an adhesive composition intermediate to drive off the water so as to yield a substantially solid adhesive composition can destabilize a bleaching agent contained therein and cause it to become less potent. Because the dental bleaching gel is generally not heated during manufacture of the bleaching compositions and devices according to the invention, greater stability and potency of the bleaching agent can be maintained.

In yet another embodiment, a dental tray or barrier strip can be coated with a flowable adhesive activation composition intermediate, such as by painting or spreading, which is then heated or allowed to dry at room temperature to form the substantially solid adhesive composition. The dental bleaching gel may then be applied to the inside surface of the dried adhesive activation composition.

The size and shape of dental bleaching compositions and devices according to the invention can be tailored to more readily fit a person's upper or lower dental arch. They may also be tailored to fit persons having differently-sized or shaped dental arches. The dental bleaching compositions and devices are advantageously designed so as to substantially cover the front and lingual surfaces of the teeth to be bleached. Bleaching both surfaces yields more esthetically appealing teeth. Moreover, bleaching both the front and lingual surfaces helps in bleaching the interproximal spaces between adjacent teeth. The dental bleaching compositions and devices are advantageously flexible and adhesive so as to A readily conform to a wide variety of differently-sized teeth and dental arches.

In one embodiment, the dental bleaching compositions and devices according to the invention are in the shape of a dental tray having a front side wall, a rear side wall, and a trough between the front and rear side walls. Having the shape of a dental tray facilitates placement of the dental bleaching composition or device over a person's teeth by minimizing the amount of manipulation that is necessary to obtain a good fit between the composition or device and the person's teeth. In another embodiment, the dental bleaching compositions and devices are in the shape of substantially flat strips or patches prior to use. Regardless of their initial shape, the inventive dental bleaching compositions and devices are designed to more reliably remain in place over the person's teeth compared to conventional bleaching strips. The result is more effective tooth bleaching and better patient compliance.

According to one embodiment, the dental bleaching composition or device has a horseshoe shape and a U-shaped trough like a conventional bleaching tray. In another embodiment, the bleaching composition or device has an L-shaped profile or "trough". It will be appreciated, however, that dental bleaching compositions and devices according to the invention can have any longitudinal profile or shape (e.g., they can be straight or have any desired degree of longitudinal curvature from one end of the composition or device to the other). The trough may have any desired cross-sectional shape (e.g., the trough can be V-shaped, trapezoidal, rectangular, or other geometric shape).

To facilitate the ability of a dental bleaching composition or device to conform to the various shapes and sizes among dental arches, the dental bleaching composition or device may include mechanical features such as a notch within the front side wall, preferably within an edge near the center of the front side wall, and/or a notch within the rear side wall, preferably within an edge near the center of the rear side wall. Notches allow a tray-like bleaching composition or device to more easily conform to differently-sized dental arches. In this way, the dental bleaching composition or device can be designed so as to be "one-size fits all."

The dental bleaching compositions and devices according to the invention can be designed to be worn for any desired time period. Increasing the concentration of dental bleaching agent within the dental bleaching gel generally reduces the required bleaching time. Nevertheless, due to the extremely comfortable fit and reliable adhesion between the inventive dental bleaching compositions and devices and the person's teeth, it is possible to wear such compositions and devices for extended periods of time in order to ensure even and thorough bleaching. Dental bleaching compositions and devices according to the invention can be designed to be worn while, e.g., talking, sleeping, eating, drinking, smiling, frowning, grimacing, yawning, coughing, smoking, or making virtually any facial expression or mouth contortion. This greatly decreases their intrusiveness into everyday activities compared to conventional bleaching strips, which do not reliably adhere to teeth, or intrusive bleaching devices such as large, bulky bleaching dental appliances.

The dental bleaching compositions or devices can be designed to be worn for as little as a few minutes or as long as several hours. By way of example, not limitation, a typical bleaching session of fast duration may last from about 10 to about 30 minutes. A bleaching session of intermediate duration may last from about 30 minutes to about 2 hours. A bleaching session of long duration, including professional bleaching or overnight bleaching while a person is sleeping, may last from about 2 hours to about 12 hours. Bleaching sessions may be repeated as many times as are needed to obtain a desired degree of whitening. In some cases, a clinical whitening effect has been observed after only 1–3 whitening sessions. A typical bleaching regimen will preferably include 1–20 bleaching sessions, more preferably 2–15 bleaching sessions, and most preferably 3–10 bleaching sessions.

For convenience of use, multiple dental bleaching compositions or devices may be packaged together and sold as a kit. In one embodiment, the number of dental bleaching compositions or devices provided with each kit can equal the number of sessions that represent a prescribed bleaching regimen. To efficiently utilize the space within a kit package, multiple dental bleaching compositions or devices can be stacked, internested, or laid together within a package. The dental bleaching compositions or devices can be sealed collectively or individually as desired. They may contain a removable protective layer on their interior surfaces to protect the adhesive composition and the dental bleaching gel from contamination or moisture, both of which can possibly cause premature decomposition of a peroxide bleaching agent.

It is within the scope of the invention to provide barrier layers, adhesive layers, and a dental bleaching gel that are initially separate and that are brought together by the end user. The adhesive composition may be a dry or substantially solid insert or it may be a liquid or gel that is applied to a barrier layer and allowed to dry prior to placement of the dental bleaching gel adjacent to the adhesive layer and placement of the finished dental bleaching device over the person's teeth.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction and Definitions

Figure 1:
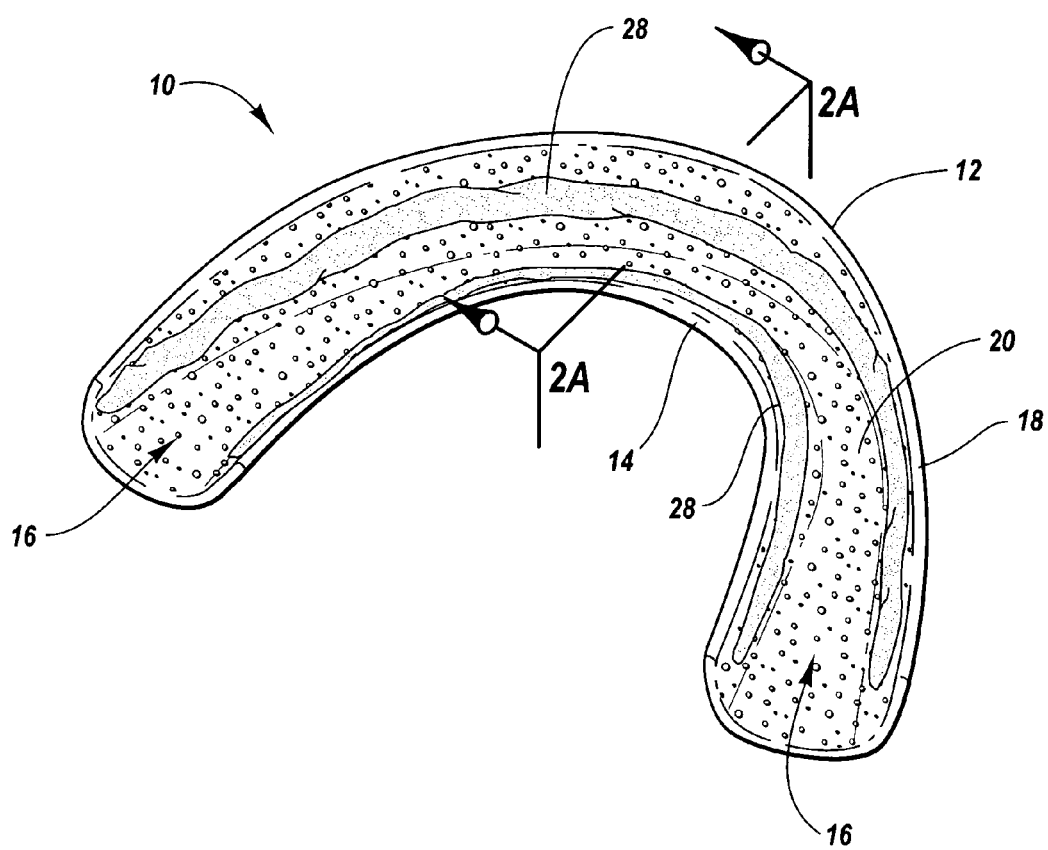
FIG. 1 is a perspective view of an exemplary dental bleaching device according to the invention in the shape of a dental tray comprising a barrier layer, an adhesive layer, and a dental bleaching gel.

The present invention generally relates to improved dental bleaching compositions and devices used to bleach a person's teeth. In one embodiment, inventive bleaching compositions include an adhesive composition that becomes more adhesive to teeth when moistened with water or saliva and a dental bleaching gel adjacent to the adhesive composition. In another embodiment, inventive dental bleaching devices include a moisture-resistant barrier layer, an adhesive composition that becomes more adhesive to teeth when moistened with water or saliva, and a dental bleaching gel adjacent to at least one of adhesive composition or barrier layer. When the bleaching composition or device is placed over a person's teeth, the adhesive composition reliably adheres to the teeth, allowing the dental bleaching gel to remain in contact with the teeth to be bleached. In addition, upon moistening the adhesive composition and/or bleaching gel, a bleaching agent activator within the adhesive composition activates the bleaching agent within the bleaching gel. The optional barrier layer protects the adhesive layer and bleaching gel from diffusing away from the person's teeth as a result of ambient saliva or moisture found within the person's mouth.

The inventive bleaching compositions and devices are more adhesive to teeth than conventional dental bleaching strips. Such compositions and devices are also less intrusive than bulky, over-the-counter, non-custom or boil-and-bite dental trays. In some ways they are as reliable, or even more reliable than, custom-fitted dental trays in maintaining a dental bleaching gel against a person's teeth. In some cases, they are also as comfortable, or even more comfortable, than custom-fitted trays.

The term "barrier layer", as used herein, refers to one or more layers of a moisture-resistant material that protects the adhesive layer and bleaching gel from ambient moisture and saliva found within a person's mouth when the dental bleaching device is placed over the person's teeth. The barrier layer may also serve to protect the adhesive layer and bleaching gel from moisture or other contaminants during storage and prior to use. The barrier layer may be in any desired form including, but not limited to, a sheet laminated to a surface of the adhesive layer, a coating applied to a pre-formed adhesive layer or bleaching composition, a dental treatment tray, or a strip or patch. The terms "strip" and "patch" are essentially synonymous.

The terms "adhesive layer", "adhesive activation layer", "adhesive composition", or "adhesive activation composition", as used herein, refer to one or more regions of a composition that has been formulated or processed so as to be substantially solid, coherent, and non-flowable. The adhesive composition may comprise a single continuous region or layer adjacent to the bleaching gel and, optionally, a barrier layer, or it may comprise a plurality of discontinuous regions or layers adjacent to a barrier layer and spaced-apart by random or predetermined intervals.

The term "substantially solid", as used herein, refers to an adhesive composition or layer that is in a solid or semi-solid condition. In one aspect, a "substantially solid" adhesive composition or layer can be characterized as a cohesive mass that does not readily flow or separate when subjected to gravitational forces and which cannot be readily expressed through a syringe outlet or other similarly-sized opening or orifice. Thus, the term "substantially solid" excludes runny adhesive liquids, viscous adhesive liquids, and even thick adhesive gels that are able to flow when subjected to gravity and/or which can be readily expressed through a syringe outlet or other similarly-sized opening or orifice. The term "substantially solid", when used in the context of an adhesive composition or layer, also excludes dry particulate adhesive compositions or powders because dry particulates and powders readily flow when subjected to gravity and/or are readily separated (i.e., the particles as a whole have little or no internal cohesion). Moreover, powders or particulates, when viewed as a whole, are not coherent or solid.

One characteristic of the "substantially solid" adhesive compositions or layers is that they become more adhesive when an exposed surface thereof is moistened with, e.g., saliva or water. When moistened, the surface of the adhesive composition or layer turns into a sticky material that is able to more strongly adhere to teeth compared to a substantially solid adhesive composition or layer that has not been moistened. The adhesive composition at the surface may become a viscous liquid, paste or gel, at least temporarily, depending on the amount of moisture that is applied to the surface of the "substantially solid" adhesive composition or layer. Nevertheless, the consistency of the moistened surface can remain "substantially solid" depending on the degree of initial moistening, or it can stiffen and even revert back to being "substantially solid" as the initial quantity of surface moisture diffuses into a remaining portion of the "substantially solid" adhesive composition or layer over time (e.g., during a bleaching procedure in which the adhesive layer or composition is protected from saliva and ambient moisture in a person's mouth by a moisture-resistant barrier layer). A characteristic of the adhesive composition or layer is that the bleaching agent activator is initially locked or retained within a solid matrix prior to moistening with saliva but which leaches, diffuses, or is otherwise made available for contacting, mixing or reacting with the bleaching gel when moistened with saliva or water in order to activate the bleaching agent and accelerate bleaching.

The term "bleaching gel", as used herein, refers to a dental bleaching composition that has been formulated or processed so as to be flowable (e.g., it can be expressed out of a syringe orifice or other dispensing means known in the art). The bleaching gels according to the invention are, however, preferably sufficiently thick or viscous that they will not run out of a dental tray or tray-like device into which the bleaching gel is placed. In one embodiment, the bleaching gel is rubbery or highly viscous. When a bleaching gel is placed next to a dry adhesive composition or layer, the two dissimilar compositions may tend to reach an equilibrium wherein some of the liquid carrier of the bleaching gel diffuses into the adhesive layer, thus further increasing the viscosity and stiffness of the bleaching gel. The bleaching gel may comprise a single continuous bead or layer adjacent to the adhesive layer, or it may comprise a plurality of discontinuous regions or layers spaced-apart by random or predetermined intervals. At least a portion of the bleaching gel may directly contact the barrier layer (e.g., through one or more discontinuities in the adhesive activation composition or layer).

The term "dental tray", as used herein, refers to any composition or device having a tray-like shape so as to facilitate placement of the composition or device over at least a portion of a person's dental arch. A "dental tray" or "tray-like" composition or device includes a front side wall configured to engage front surfaces of a person's teeth when in use, a rear side wall extending laterally from the front side wall, either abruptly by one or more distinct angles or non-abruptly by a curved transition portion, configured to engage lingual surfaces of the person's teeth, and a trough between said front and rear side walls. A "dental tray" may be configured so that a portion of the front side wall, rear side wall, or a transition portion thereof (e.g., a bottom wall), engages the incisal or occlusal edges of the person's teeth when in use. The dental tray may be curved or straight in a longitudinal dimension.

The term "trough", as used herein, refers to the region that is at least partially bounded by the front side wall, the rear side wall, and a plane or imaginary curved dome extending from an upper edge of the front side wall and an upper edge of the rear side wall. Thus, a "trough" can theoretically exist whenever the front and rear side walls have a space therebetween and are laterally offset by an angle of less than 180°. In practice, the front and rear side walls will be offset by an angle that is preferably less than about 150°, more preferably less than about 120°, and most preferably less than about 90°.

In the case where the front and rear side walls are connected by a transition portion (e.g., a trough having a U-shaped or rectangular cross section), at least a portion of the front and rear side walls may be substantially parallel (i.e., be offset by an angle of approximately 0°) or offset by a very small angle. In the case of a trough having a V-shaped or trapezoidal cross section, at least a portion of the front and rear side walls may be offset by an acute angle (i.e., by an angle between 0–90°). In the case of a trough having an L-shaped cross section, at least a portion of the front and rear side walls may be offset by an angle centered around approximately 90° (e.g., by an angle in a range of about 70° to about 110°). Thus, a trough having an L-shaped cross section can be a subset or slight variation of a trough having a V-shaped cross section.

The terms "longitudinal", "longitudinal dimension" and "longitudinal profile", as used herein when referring to a dental tray or treatment device, shall refer to the lengthwise dimension of the tray or device. The tray or device may be straight in the "longitudinal dimension" or it may be horseshoe-shaped or otherwise "longitudinally curved" in the longitudinal dimension so as to approximate the curvature of a person's dental arch, or at least facilitate placement of the tray or device over the dental arch.

The terms "shaped bleaching composition", "shaped bleaching device" and "shaped adhesive composition", as used herein, refer to a composition that has been formulated or processed so that at least a portion of the composition is substantially solid, coherent, and non-flowable. The "shape" of the adhesive layer, bleaching composition, or bleaching device is primarily determined by the shape and relative rigidity of the barrier layer and/or adhesive layer. The bleaching gel typically does not determine or contribute to the "shape" of the bleaching compositions and devices but conforms to the shape of the adhesive layer and/or barrier layer.

The terms "strip" or "patch" are used interchangeably and shall refer to any bleaching composition or device that is substantially flat, or that has a slight curvature or bend but that does not constitute a "dental tray", as that term is understood in the art. A "strip" or "patch", with or without a barrier layer, includes an inner surface or region configured to engage the front and/or rear surfaces of a person's teeth and/or gums when in use and an outer surface that is generally oriented away from the person's teeth and/or gums. A "strip" or "patch" may be configured so that a portion of the inner surface engages the incisal or occlusal edges of the person's teeth when in use. The strip or patch may be curved or straight in one or both of the lengthwise and widthwise directions in order to fit over a user's teeth and/or gums in a desired manner.

The term "molecular weight", as used herein, shall refer to number average molecular weight expressed in Daltons, unless otherwise specified.

II. Dental Bleaching Compositions and Devices

The dental bleaching compositions according to the invention can exist alone or in combination with a barrier layer as part of a dental bleaching device. Dental bleaching compositions according to the invention include an adhesive composition that becomes more adhesive to teeth when moistened by, e.g., saliva or water, and a dental bleaching gel, often adjacent to the adhesive composition. Dental bleaching devices according to the invention further include a moisture-resistant barrier layer protects the adhesive composition and bleaching gel from ambient moisture within a person's mouth during use. Following are preferred examples of barrier layers, adhesive layers, and bleaching gels according to the invention, as well as characteristics of bleaching compositions or devices made therefrom.

A. Barrier Layers

According to one embodiment of the invention, the barrier layer comprises a thin, flexible membrane formed from a moisture-resistant polymer material. In one embodiment, the barrier layer comprises a thin, flexible layer of a polyolefin or similarly moisture-resistant material, such as wax, metal foil, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes, or polyesteramides. Such materials may be provided in the form of large, flat, flexible sheets to which an adhesive composition or layer is applied. Alternatively, such sheets may be applied or attached to an existing adhesive composition or a bleaching composition comprising a substantially solid adhesive layer and a bleaching gel.

Notwithstanding the foregoing, it is within the scope of the invention to provide barrier layers having any desired material, thickness or rigidity so long as the barrier layer provides at least some moisture protection relative to the adhesive composition or layer and bleaching gel. The barrier layer may comprise a conventional dental tray, examples of which include both customized and non-custom dental trays, or it may initially be a strip or patch, or have some other configuration. The barrier layer may be as simple as a layer of a moisture resistant material that is sprayed or painted on, applied by dipping, or otherwise applied to an existing shaped adhesive or bleaching composition (e.g., one that is in the form of a dental tray or that otherwise has a desired shape).

Examples of suitable polyolefins for use in making the barrier layer include, but are not limited to, polyethylene (PE), high density polyethylene (HDPE), low density polyethylene (LDPE), ultra low density polyethylene (ULDPE), polypropylene (PP), and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. An example of a suitable polyurethane barrier material is a polyurethane film manufactured by ArgoTech, which is located in Greenfield, Mass. Plasticizers, flow additives, and fillers known in the art can be used as desired to modify the properties of any of the foregoing polymers used to form the barrier layer.

According to one embodiment, the barrier layer is formed of a mixture of ethylene-vinyl acetate copolymer (EVA) and polypropylene (PP), preferably comprising about 5% to about 35% PP, more preferably about 10% to about 30% PP, more especially preferably about 15% to about 25% PP, and most preferably about 20% PP, with the balance comprising ethylene-vinyl acetate (EVA), and optionally other polymers and/or small quantities of additives such as plasticizers.

It is also within the scope of the invention to utilize barrier layers that are formed onto a surface of a previously formed adhesive layer or bleaching composition, such as by adhering a sheet or tray-like barrier layer to the adhesive layer or bleaching composition. Alternatively, the barrier layer may itself be initially flowable and later hardened, such as a lacquer that contains a barrier material (e.g., a cellulosic ether, cellulose acetate, wax, plastic, polyvinyl acetate, polyvinyl alcohol, or shellac) dissolved in one or more solvents that are later removed; a chemical or light-cure material (e.g., a methacrylate or acrylate resin); or a thermoplastic melt (e.g., any thermoplastic resin). Examples of useful cellulosic ethers that can be used to form a barrier layer include, but are not limited to, ethyl cellulose, propyl cellulose, isopropyl cellulose,.butyl cellulose, t-butyl cellulose, and the like.

B. Adhesive Compositions and Layers

Prior to being moistened in preparation for or during use, adhesive compositions and layers within dental bleaching compositions and devices according to the invention preferably comprise a substantially solid and coherent adhesive composition, as opposed to a liquid, a flowable gel, or a dry powder or particulate. The adhesive composition or layer may comprise a single coherent mass or region, or it may comprise a plurality of coherent masses or regions. Providing a substantially solid and coherent adhesive composition or layer better maintains the dental bleaching gel against the teeth being bleached instead of diffusing into the surrounding oral cavity, as compared to bleaching gels that are loaded without an adhesive layer into customized or non-customized dental trays or that are applied using bleaching strips without an adhesive layer. This, in turn, promotes better tooth whitening and patient compliance by reducing irritation to surrounding oral tissues and/or at least some of the bad taste normally associated with dental bleaching.

Substantially solid adhesive compositions include at least one tooth adhesion agent and, optionally, one or more inert component or active agents. In the case where an active agent is included, it may be advantageously dispersed within a substantially solid matrix comprising the tooth adhesion agent. Alternatively, an active agent in the form of a liquid or solution can be spread, sprayed, or otherwise applied to the inner surface of the adhesive composition prior to or after applying the bleaching gel thereto. Following are preferred tooth adhesion agents and bleaching agent activators, as well as exemplary inert components and active agents that may optionally be included within the adhesive composition.

1. Tooth Adhesion Agents

The tooth adhesion agent may comprise any known tackifying agent that is substantially non-adhesive, or less adhesive, when the adhesive composition or layer is substantially solid but which becomes more adhesive to teeth when the adhesive composition or layer is moistened with, e.g., water or saliva. A presently preferred tooth adhesion agent is polyvinyl pyrrolidone (PVP). PVP polymers have been found to provide excellent adhesion to polymer barrier layers made from PE, PET, polyurethane, and paraffin, to be substantially non-adhesive when the adhesive composition is dry to the touch, and to have superior adhesion to teeth when a surface of a substantially solid adhesive composition is moistened with saliva or water.

Non-limiting examples of polyvinyl pyrrolidone polymers that have been used in formulating adhesive compositions and layers according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million. Because PVP polymers having widely varying molecular weights have been found to provide similar adhesion and wetting properties, it is believed that PVP polymers of any molecular weight, at least those having a molecular weight between 50,000 and 1.3 million, will be useful in formulating substantially solid adhesive compositions or layers according to the invention.

Other tooth adhesion agents that may be used in addition to, or instead of, PVP within the scope of the invention include, but are not limited to, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like.

Although polyethylene oxide polymers comprises a less preferred tooth adhesion agent, it has been found that a polyethylene oxide polymer having a molecular weight of 1 million provides better adhesion to barrier layers such as MYLAR than a polyethylene oxide polymer having a molecular weight of 100,000.

The one or more tooth adhesion agents are preferably included in an amount in a range of about 10% to about 90% by weight of the substantially solid adhesive composition (exclusive of any bound water or other solvent), more preferably in a range of about 20% to about 80% by weight of the substantially solid adhesive composition, and most preferably in a range of about 40% to about 75% by weight of the substantially solid adhesive composition.

2. Bleaching Agent Activators

The adhesive compositions and layers may comprise any known bleaching agent activator that is capable of destabilizing a dental bleaching agent in order to accelerate bleaching. When peroxides are destabilized they more rapidly release oxygen radicals, which cause tooth bleaching. The bleaching agent activator is advantageously retained within the substantially solid adhesive composition prior to use (e.g., is locked within a substantially solid matrix), but which diffuses, leaches, or otherwise contacts, mixes or reacts with the bleaching gel upon moistening the dental bleaching gel and/or adhesive composition with saliva or water. In one embodiment, the bleaching gel is initially substantially anhydrous and/or does not initially touch the adhesive composition in order to prevent diffusion or leaching of the bleaching agent activator into the bleaching gel prior to use.

One class of bleaching agent activators includes bases (i.e., substances that raise the pH in aqueous systems). Examples of useful bases that can destabilize bleaching agents and thereby accelerate bleaching include oxides, hydroxides, carbonates, and bicarbonates of alkali metals and alkaline earth metals, and amines. Non-limiting examples include sodium oxide, sodium hydroxide, potassium oxide, potassium hydroxide, sodium carbonate, sodium bicarbonate, ammonium hydroxide, magnesium hydroxide, sodium phosphate tribasic, and ethanolamine. Bases, when used as bleaching agent activators, are preferably included in an amount in a range of about 0.1% to about 20% by weight of the adhesive composition, more preferably in a range of about 1% to about 10% by weight, and most preferably about 7% by weight.

Another class of bleaching agent activators includes metals and metal compounds. Examples of metals and metal compounds include transition metals (e.g., powders or fine particulates of iron, cobalt, nickel, copper, zinc, manganese, chromium, and the like) or metal compounds (e.g., halides or sulfates of iron, cobalt, nickel, copper, zinc, manganese, chromium, and the like). More specific examples include iron and manganese metal, manganese chloride, manganese citrate, ferrous sulfate, and manganese sulfate.

Another class of bleaching agent activator includes enzymes, particularly organo-metallic enzymes containing transition metals, such as iron. One example is "catalase", which is described more particularly in U.S. Pat. No. 6,485,709 to Banerjee et al.

Metals, metal compounds, and organo-metallic enzymes, when used as a bleaching agent activator, are preferably included in an amount in a range of about 0.01% to about 20% by weight of the adhesive composition, more preferably in a range of about 0.05% to about 10% by weight, and most preferably in a range of about 0.1% to about 5% by weight.

3. Inert Components

The adhesive compositions and layers may include inert components in addition to the tooth adhesion agent and bleaching agent activator, as desired, to yield a final composition or layer having desired properties. Examples of "inert" components include, but are not limited to, plasticizers and humectants (e.g., glycerin, sorbitol, polyethylene glycol, propylene glycol, and polypropylene glycol), volatile solvents (e.g., water and alcohols, such as ethanol), stabilizing agents (e.g., EDTA and citric acid), neutralizing agents (e.g., sodium hydroxide), thickening agents (e.g., fumed silica), flavorants, sweeteners, and the like.

When water is used as a solvent when manufacturing adhesive compositions or layers according to the invention and then driven off by evaporation to yield a substantially solid dental bleaching or desensitizing composition, it is postulated that a significant amount of water remains bound or associated with the hydrophilic components within the adhesive composition, including the tooth adhesion agent, any inert components (e.g., polyols added as humectants, stabilizing agents, neutralizing agents, and/or thickening agents), and any hydrophilic active agents (e.g., bleaching and/or desensitizing agents). Although the amount of residual water has not yet been determined, it is believed that approximately 10% of the water added initially remains after the initially flowable adhesive composition intermediate has been dried sufficiently to yield the substantially solid adhesive composition or layer.

4. Active Agents

A wide, variety of active agents known in the dental and oral arts can be included within the adhesive composition or layer. Examples of active agents include desensitizing agents (e.g., potassium nitrate), remineralizing agents (e.g., sodium fluoride or other fluoride salts), antimicrobial agents (e.g., chlorhexidine), antiplaque agents, anti-tartar agents, or other medicaments.

Examples of substantially solid adhesive compositions and layers that include one or more active agents are disclosed in U.S. application Ser. No. 10/446,235, filed May 27, 2003; U.S. application Ser. No. 10/446,471, filed May 27, 2003; U.S. application Ser. No. 10/637,237, filed Aug. 8, 2003; U.S. application Ser. No. 10/646,484, filed Aug. 22, 2003; and U.S. application Ser. No. 10/646,443, filed Aug. 22, 2003. For purposes of disclosing solid adhesive compositions and layers that include one or more active agents, the foregoing applications are incorporated herein by reference.

When one or more bleaching agents are included within the substantially solid adhesive composition, they are preferably included in an amount in a range of about 5% to about 80% by weight of the substantially solid adhesive composition, more preferably in a range of about 10% to about 60% by weight of the substantially solid adhesive composition, and most preferably in a range of about 20% to about 50% by weight of the substantially solid adhesive composition.

When potassium nitrate is included within the substantially solid adhesive composition as a desensitizing agent, it is preferably included in an amount in a range of about 0.01% to about 50% by weight of the substantially solid adhesive composition, more preferably in a range of about 0.1% to about 25% by weight of the substantially solid adhesive composition, and most preferably in a range of about 0.5% to about 10% by weight of the substantially solid adhesive composition.

For treating periodontal disease, chlorhexidine gluconate is a preferred medicament and is preferably included in an amount in a range of about 0.01 to about 50% by weight of the substantially solid adhesive composition, more preferably in a range of about 0.05% to about 25% by weight of the substantially solid adhesive composition, and most preferably in a range of about 0.1% to about 10% by weight of the substantially solid adhesive composition. Other antibacterial agents or medicaments may be included in the same concentration ranges.

C. Bleaching Gels

The bleaching compositions and devices according to the invention may include any bleaching gel known in the art. The bleaching gel may comprise a continuous layer or bead positioned so as to cover a person's front tooth surfaces, rear tooth surfaces, or both, or it may comprise separate beads, layers or islands of gel separated by a space. Preferred bleaching gels are those that are substantially viscous and tacky in order to assist the adhesive layer in retaining the bleaching composition or device against a person's teeth during use. In one embodiment, the bleaching gels according to the invention may comprise at least one bleaching agent and any of the adhesive composition intermediates used to manufacture the substantially solid adhesive compositions or layers described herein (exclusive of the bleaching agent activator).

Exemplary dental bleaching gels, and methods for making such gels, which may be used to manufacture the bleaching compositions and devices according to the invention are disclosed in U.S. Pat. Nos. 5,376,006; 5,785,527; 5,851,512; 5,858,332; 5,985,249; 6,306,370; 6,309,625; 6,312,671; 6,322,774; 6,368,576; 6,387,353; 6,500,408; and 6,503,485. For purposes of disclosing dental bleaching gels, and methods of making such gels, the foregoing patents are incorporated herein by reference.

In general, the dental bleaching gels will include at least one dental bleaching agent, at least one tackifying agent, and a liquid or gel carrier or vehicle into which the dental bleaching agent and tackifying agent are dispersed. The bleaching gel may optionally include other active agents (e.g., desensitizing agents, remineralizing agents, antimicrobial agents, and the like). An advantage of providing a bleaching gel separate from the adhesive layer is that it provides a bleaching composition or device that is more stable or consistent relative to the amount of active bleaching agent. Heating an adhesive composition intermediate to drive off the water so as to yield a substantially solid adhesive composition can destabilize a bleaching agent contained therein and render it less potent. Because the dental bleaching gel is generally not heated during manufacture of bleaching composition and devices according to the invention, greater stability and potency of the bleaching agent may be achieved. According to one embodiment, the bleaching gel is initially substantially anhydrous in order to prevent, inhibit or minimize diffusion or leaching of the bleaching agent activator from the adhesive composition or layer into the bleaching gel. In another embodiment, the bleaching device is manufactured in a manner so that the bleaching gel directly contacts the barrier layer but not the adhesive composition, thereby preventing or inhibiting premature activation of the bleaching gel. Following are preferred bleaching agents, tackifying agents, and carriers or vehicles.

1. Bleaching Agents

A common dental bleaching agent that is known to bleach teeth and that has been found to be safe for oral use is hydrogen peroxide. However, hydrogen peroxide does not itself exist free in nature, but only as an aqueous solution or as a complex. Aqueous hydrogen peroxide is an acceptable dental bleaching agent to the extent that an anhydrous bleaching gel is not desired. Non-limiting examples of complexed hydrogen peroxide include carbamide peroxide and metal perborates. Other bleaching agents that can be used to bleach teeth include, but are not limited to, metal percarbonates, peroxides, chlorites, and hypochlorites, peroxy acids, and peroxy acid salts.

Bleaching agents within the dental bleaching gels according to the invention can have any desired concentration, e.g., between 1–90% by weight of the dental bleaching gel. The concentration of the dental bleaching agent can be adjusted depending on the intended treatment time for each bleaching session. In general, the shorter the treatment time, the more bleaching agent will be added to accelerate dental bleaching so as to effect bleaching in a shorter time period.

The one or more bleaching agents are preferably included in an amount in a range of about 1% to about 60% by weight of the dental bleaching gel, more preferably in a range of about 3% to about 40% by weight of the dental bleaching gel, and most preferably in a range of about 5% to about 30% by weight of the dental bleaching gel.

2. Tackifying Agents

Useful tackifying agents that may be used in the bleaching gel include any of the tooth adhesion agents disclosed herein for use in manufacturing the substantially adhesive compositions or layers according to the invention. The main difference between a "tackifying agent" within a "bleaching gel", and a "tooth adhesion agent" within an "adhesive composition" or "adhesive layer" is the physical state. On the one hand, a tackifying agent within a bleaching gel is already mixed with a liquid or gel carrier or vehicle such that the resulting dental bleaching gel is immediately sticky and tacky to the touch as a result of the tackifying agent. On the other hand, an adhesive composition or layer typically becomes much more adhesive to teeth when the adhesive composition or layer is moistened by saliva or water as a result of the tooth adhesion agent. The adhesive composition or layer may initially be non-adhesive and dry to the touch prior to moistening with saliva or water.

One useful tackifying agent is polyvinyl pyrrolidone (PVP). Non-limiting examples of polyvinyl pyrrolidone polymers that have been used in formulating dental bleaching gels according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million.

Other useful tackifying agents that may be used in addition to, or instead of, PVP within the scope of the invention include, but are not limited to, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like.

The one or more tackifying agents are preferably included in an amount in a range of about 1% to about 50% by weight of the dental bleaching gel, more preferably in a range of about 3% to about 30% by weight of the dental bleaching gel, and most preferably in a range of about 5% to about 20% by weight of the dental bleaching gel.

3. Carriers and Vehicles

The dental bleaching gel will typically include one or more liquid or gel carriers or vehicles into which the dental bleaching agent, tackifying agent, and other components are dispersed. Examples of liquid or gel carriers or vehicles include, but are not limited to, water, alcohols (e.g., ethyl alcohol), and polyols (e.g., glycerin, sorbitol, polyethylene glycol, polyethylene oxide, propylene glycol, and polypropylene glycol). The carrier or vehicle will typically comprise the balance of components in the dental bleaching gel in (addition to the bleaching agent, tackifying agent, and any other components.

4. Other Components

The dental bleaching gels according to the invention may optionally include other components as desired to yield a bleaching gel having desired properties. Examples include stabilizing agents (e.g., EDTA), neutralizing agents (e.g., sodium hydroxide), thickening agents (e.g., fumed silica), desensitizing agents (e.g., potassium nitrate, other potassium salts, citric acid, citrates, and sodium fluoride), remineralizing agents (e.g., sodium fluoride, stannous fluoride, sodium monofluorophosphate, and other fluoride salts), antimicrobial agents (e.g., chlorhexidine, troclosan, and tetracycline), antiplaque agents, anti-tartar agents (e.g., pyrophosphates salts), other medicaments, flavorants, sweeteners, and the like.

D. Characteristics of Dental Bleaching Compositions and Devices

In one embodiment, the dental bleaching compositions and devices according to the invention are preferably in the shape of a dental tray having a front side wall, a rear side wall, and a trough between the front and rear side walls. Having the shape of a dental tray facilitates placement of the dental bleaching composition or device over a person's teeth by reducing the amount of manipulation that is necessary to obtain a good fit between the composition or device and the person's teeth. In another embodiment, the bleaching compositions and devices are in the shape of a patch or strip. It is within the scope of the invention for the bleaching compositions and devices to have any desired shape or configuration.

Dental bleaching compositions and devices that have a substantially solid adhesive layer that becomes more adhesive when moistened with water or saliva, are easier to install over a person's teeth compared to conventional bleaching strips or patches, which do not reliably adhere to a user's teeth. That is because the inventive dental bleaching compositions and devices are designed to more reliably adhere and remain in place over the person's teeth compared to conventional bleaching strips, which employ a dental bleaching gel immediately adjacent to a plastic sheet. The result is more effective tooth bleaching and better patient compliance. In contrast to conventional bleaching strips, which are not recommended for use while a person eats, drinks, smokes or sleeps, dental bleaching compositions and devices according to the invention can be designed so as to be worn while talking, sleeping, eating, drinking, smiling, frowning, grimacing, yawning, coughing, smoking, or making virtually any facial expression or mouth contortion.

Figure 2A:
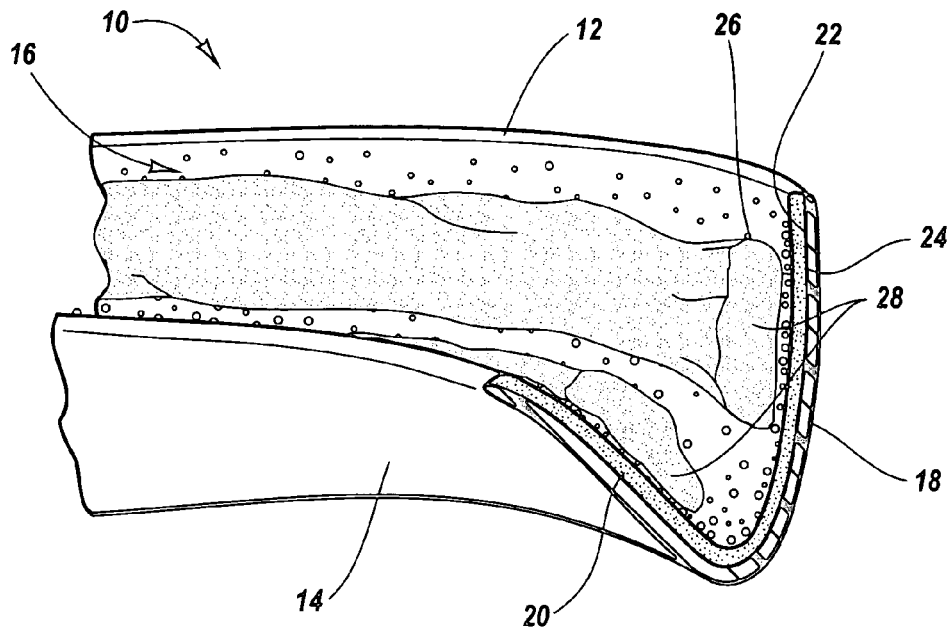
FIG. 2A is a cross-sectional view of the dental bleaching device depicted in FIG. 1.

According to one embodiment, the dental bleaching compositions and devices have a horseshoe shaped longitudinal profile and a trough with a U-shaped cross section, much like a conventional bleaching tray. An exemplary dental bleaching device in the form of a dental tray is depicted in FIGS. 1 and 2A. FIG. 1 is a perspective view of a dental bleaching device 10 having a front side wall 12 and a rear side wall 14 that together have a generally horseshoe shape in a longitudinal dimension and that define a trough 16 having a generally U-shaped cross section. The U-shaped cross section of the trough is seen more clearly in FIG. 2A.

The dental bleaching device 10 further includes a barrier layer 18, preferably comprising a moisture-resistant material, an adhesive composition or layer 20, preferably comprising a substantially solid adhesive composition, and a dental bleaching gel 28. As best seen in FIG. 2A, the adhesive layer 20 includes an outer surface 22, which is adjacent to an interior surface 24 of the barrier layer 18, and an inner surface 26, which is adjacent to the dental bleaching gel 28. It is within the scope of the invention for the bleaching gel 28 to directly contact the adhesive layer 20, the barrier layer 18, or both depending on where the bleaching gel 28 is located relative to the adhesive layer 20. In one embodiment, both the dental bleaching gel 28 and a portion of the inner surface 26 of the adhesive layer 20 are designed to directly contact a person's teeth when the dental bleaching device 10 is in use. An upper edge of the front side wall 12 can be designed so as to terminate at or shy of the gingival margin of a person's dental arch when the dental bleaching device 10 is in use.

Figure 2B:
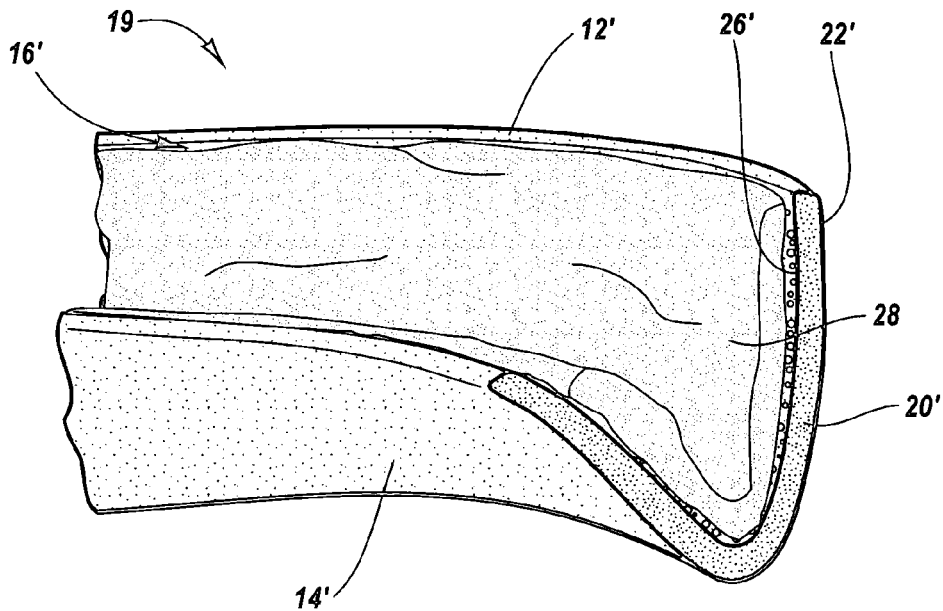
FIG. 2B is a cross-sectional view of en exemplary dental bleaching composition according to the invention in the shape of a dental tray, but without a barrier layer.

FIG. 2B alternatively depicts a dental bleaching composition 19 comprising an adhesive composition or layer 20' in the shape of a dental tray, so as to have a front side wall 12' and a rear side wall 14', and a dental bleaching gel 28 adjacent to an inner surface 26' of the adhesive layer 20'. The dental bleaching composition 19 differs from the dental bleaching device 20 of FIGS. 1 and 2A in that it includes no barrier layer. The adhesive layer 20' also includes an exterior surface 22' that may optionally be coated with a water-resistant barrier layer or material if desired (see FIG. 2A) to protect the dental bleaching composition (more particularly the adhesive layer 20' and dental bleaching gel 28) from saliva or ambient moisture (see FIG. 2A). The dental bleaching composition 19 may be sold alone or together with a moisture-resistant barrier layer, or a material used to make a barrier, that can be placed adjacent to the exterior surface 22' of the adhesive layer 20' prior to or during use.

Figure 2C:
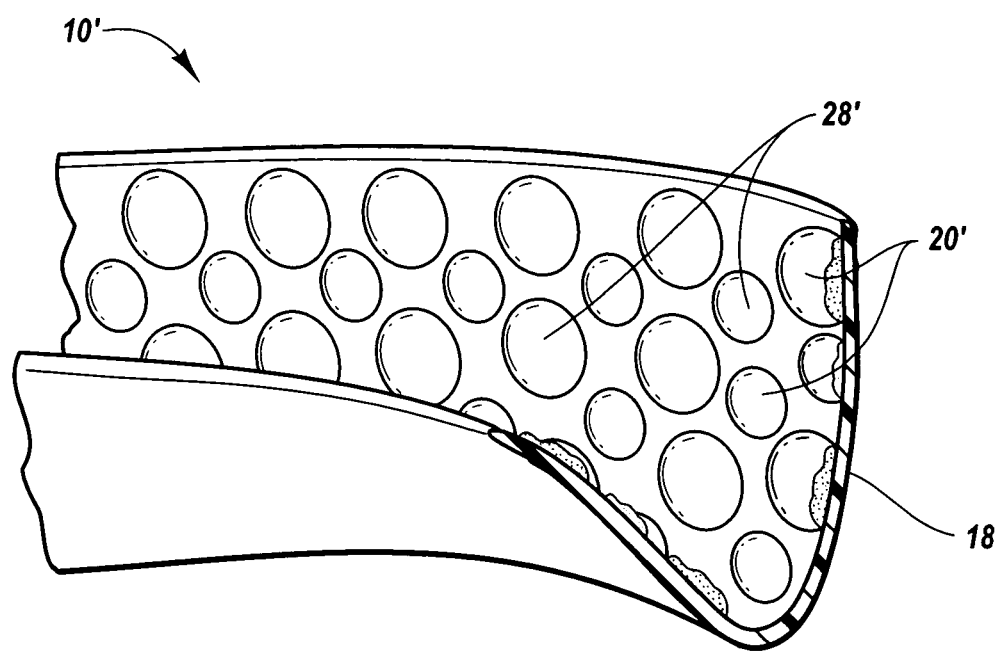
FIG. 2C is a cross-sectional view of an exemplary bleaching device according to the invention that includes a barrier layer and multiple spots or regions of adhesive composition interspersed with multiple spots or regions of bleaching gel.

FIG. 2C alternatively depicts a dental bleaching device 10' that includes a barrier layer 18, regions or spots of an adhesive composition 20' interspersed with regions or spots of a dental bleaching gel 28'. Both the adhesive composition 20' and dental bleaching gel 28' are located adjacent to the barrier layer. In this way, the adhesive composition 20' and dental bleaching gel 28' do not initially touch prior to use, thereby preventing or inhibiting contact between the bleaching agent activator within the adhesive composition 20' and the bleaching agent within the bleaching gel 28' prior to use.

Figure 3:
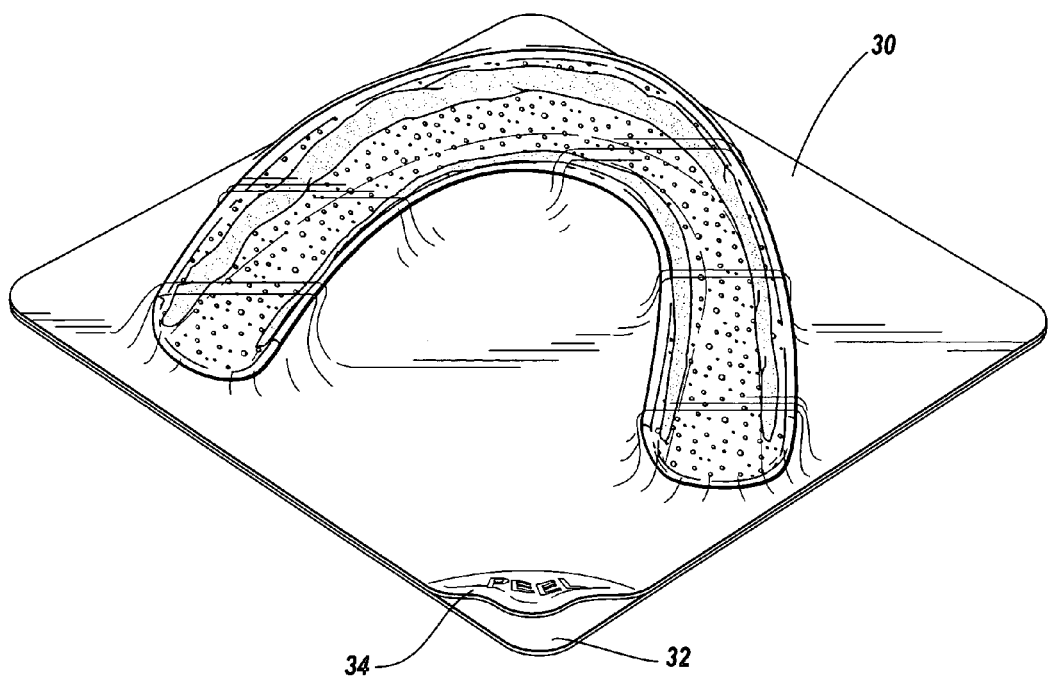
FIG. 3 illustrates a dental bleaching composition or device according to the invention contained within a sealed protective package having a peelable cover.

In order to protect dental bleaching compositions or devices according to the invention from contaminants during storage and prior to use, the bleaching compositions or devices can be packaged within a sealed container or package. As illustrated in FIG. 3, a bleaching device or bleaching composition according to the invention can be sealed within a protective package 30 that includes a rigid support layer 32 and a peelable cover 34. When it is desired to use the bleaching device or composition, the peelable cover 34 is removed and the bleaching device or composition is removed or separated from the support layer 32. In addition to, or instead of, the protective package 30, the bleaching device or composition may alternatively include a removable protective layer (not shown) that is temporarily placed within the trough adjacent to the dental bleaching gel. When it is desired to use the bleaching device or composition, the removable protective layer is removed so as to expose the bleaching gel.

Figure 4:
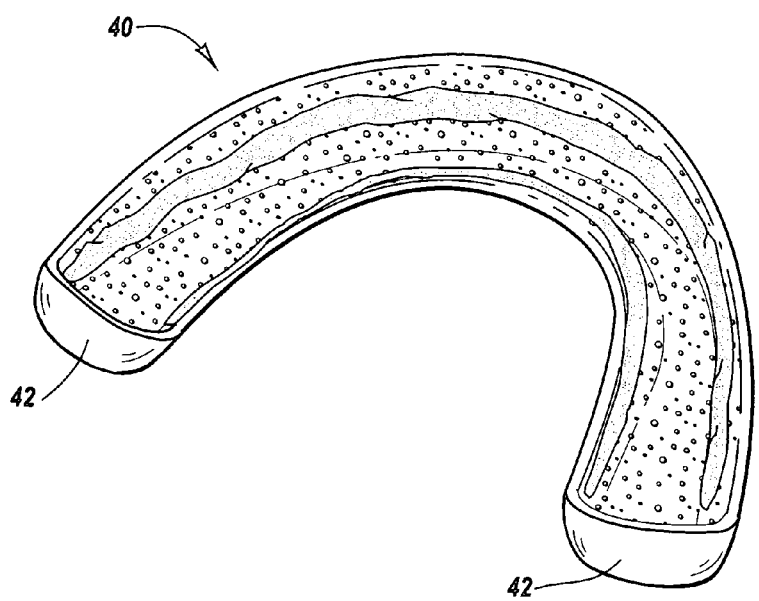
FIG. 4 is a perspective view of an exemplary dental bleaching composition or device that is similar to the bleaching device depicted in FIG. 1, or the bleaching composition of FIG. 2B, but that further includes a terminal side wall on each longitudinal end.

FIG. 4 illustrates a dental bleaching composition or device 40 that is a variation of the U-shaped dental bleaching device 10 of FIGS. 1 and 2A or the dental bleaching composition 19 of FIG. 2B. The main difference is that each longitudinal end 42 of the dental bleaching composition or device 40 is raised so as to at least partially enclose the last tooth on each side of a person's dental arch when the bleaching composition or device 40 is in use.

Figure 5:
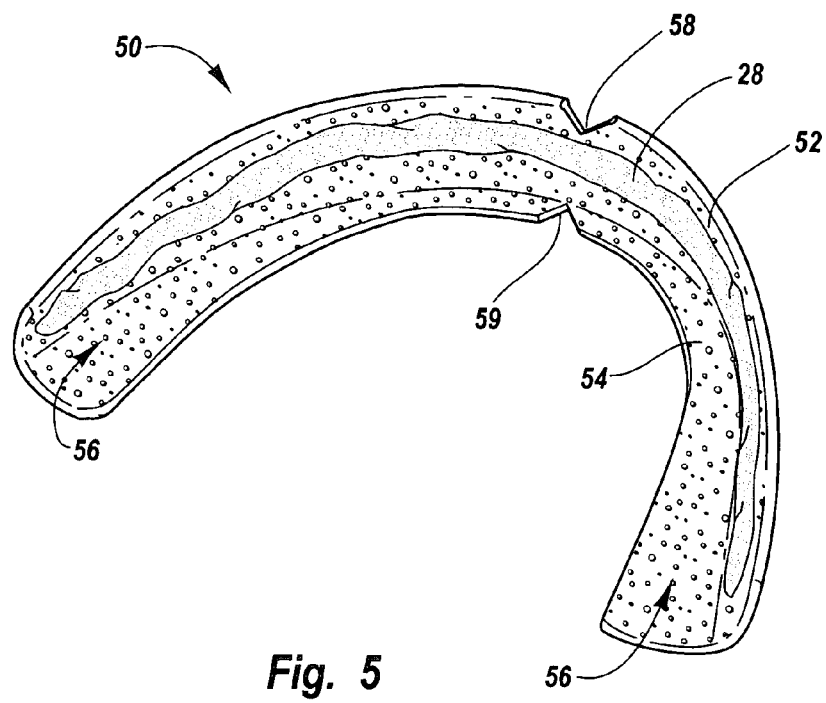
FIG. 5 is a perspective view of an exemplary dental bleaching composition or device having an L-shaped trough and a curved longitudinal profile.

FIG. 5 illustrates an alternative embodiment of a dental bleaching composition or device 50 according to the invention that has an L-shaped cross section. More particularly, the dental bleaching composition or device 50 includes a front side wall 52 and a rear side wall 54 extending laterally from the front side wall 52 so as to form a trough 56 having an approximate L-shaped cross section. The L-shaped bleaching composition or device 50 of FIG. 5 is somewhat easier to initially place over a person's dental arch compared to the U-shaped bleaching composition or devices of FIGS. 1–4. This is due to the approximately planar orientation of the rear side wall 54 relative to the occlusal or incisal edges of a person's teeth when the front side wall 52 of the dental bleaching composition or device 50 is initially placed and adhered against the front surfaces of a person's teeth. On the other hand, more manipulation of the L-shaped bleaching composition or device 50 is generally required to form and adhere the rear side wall 54 against the lingual surfaces of the person's teeth as a result of the greater initial offset angle between the front side wall 52 and rear side wall 54. However, the ability of dental bleaching compositions or devices according to the invention to adhere to tooth surfaces immediately after placement over a person's teeth, and even more so after initial wetting of the adhesive layer, facilitates the process of conforming the front side wall 52 and rear side wall 54 to the person's tooth surfaces.

In the case of the dental bleaching composition or device 50 having an L-shaped cross section, it may be more correct to say that the rear side wall 54 extending laterally from the front side wall 52 is really a bottom wall rather than a rear side wall. Nevertheless, because this erstwhile "bottom wall" of an L-shaped bleaching composition or device is folded back against the lingual tooth surfaces during use, it can be readily seen that a bleaching composition or device having an L-shaped trough is merely a variation of a composition or device having a V-shaped trough. Thus, for purposes of this disclosure and the appended claims, the side wall 54 shall constitute, and fall within the definition of, a "rear side wall".

To facilitate the ability of a dental bleaching composition or device to conform to the varying shapes and sizes among dental arches, the dental bleaching composition or device may include mechanical features such as one or more notches within the front or rear side walls. As shown in FIG. 5, the dental bleaching composition or device 50 includes a notch 58 in an outer edge near the center of the front side wall 52 and a notch 59 in an outer edge near the center of the rear side wall 54. Notches 58 and 59 allow the tray-like bleaching composition or device to more easily spread open or compress when being conformed to differently-sized dental arches. In this way, the dental bleaching composition or device 50 can more easily be a "one-size fits all" composition or device.

Figure 6:
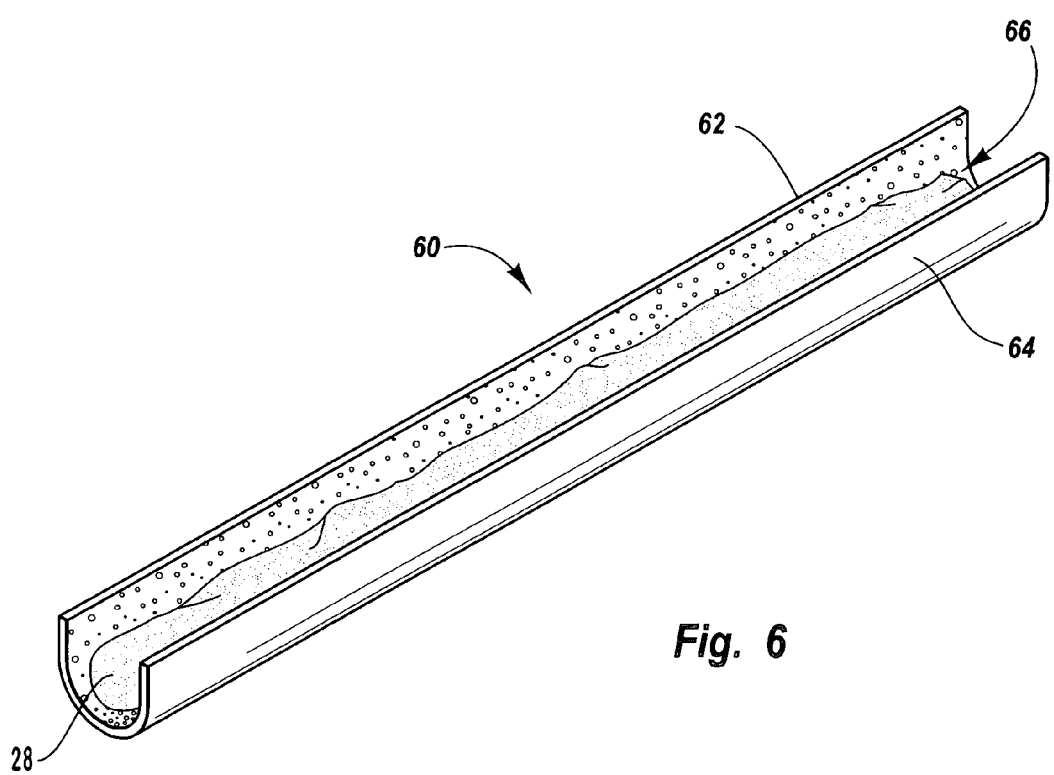
FIG. 6 is a perspective view of an exemplary dental bleaching composition or device having a U-shaped trough and a substantially straight longitudinal profile.

FIG. 6 depicts an alternative embodiment of a dental bleaching composition or device 60 according to the invention, which includes a front side wall 62 and a rear side wall 64 that define a U-shaped trough 66 into which a bead of bleaching gel 28 is placed. Instead of being horseshoe shaped like the dental bleaching composition or device of FIGS. 1–5, or otherwise having a curved longitudinal profile, the dental bleaching composition or device 60 of FIG. 6 has a substantially straight or linear longitudinal profile.

Figure 7:
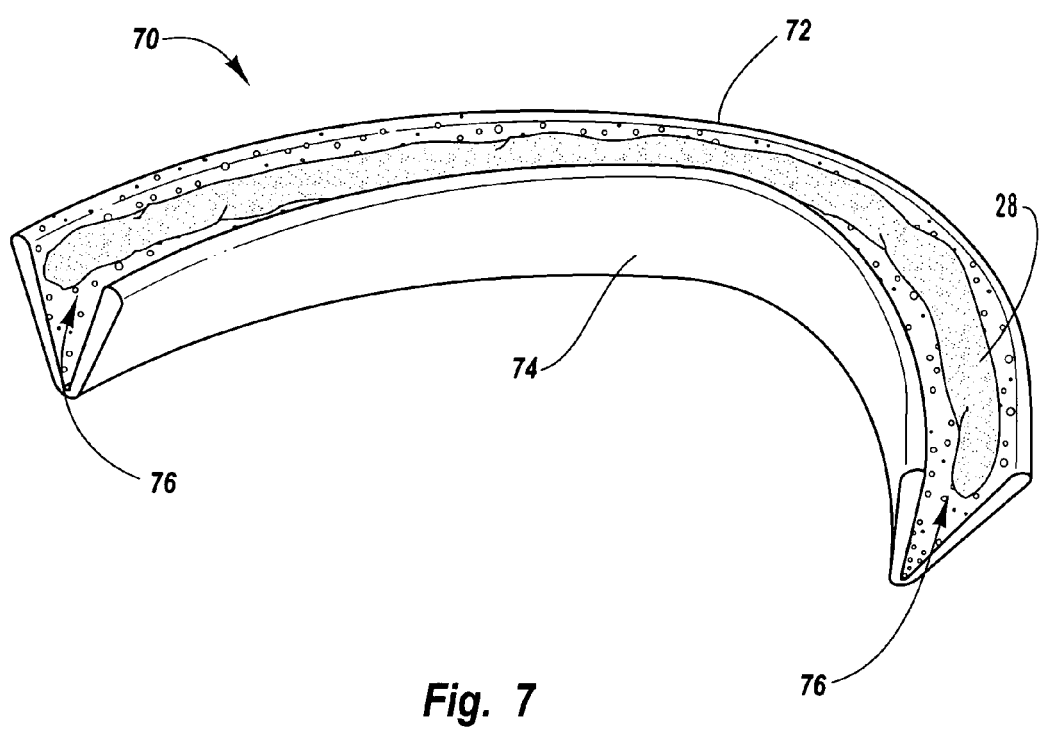
FIG. 7 is a perspective view of an exemplary dental bleaching composition or device having a V-shaped trough and a curved longitudinal profile.

FIG. 7 depicts yet another alternative embodiment of a dental bleaching composition or device 70 according to the invention. The dental bleaching composition or device 70 includes a front side wall 72 and a rear side wall 74 that define a V-shaped trough 76 and a curved longitudinal profile. The main difference between the V-shaped bleaching composition or device 70 of FIG. 7 and the L-shaped bleaching composition or device 50 of FIG. 5 is the angle at which the front and rear side walls are laterally offset from each other.

Figure 8:
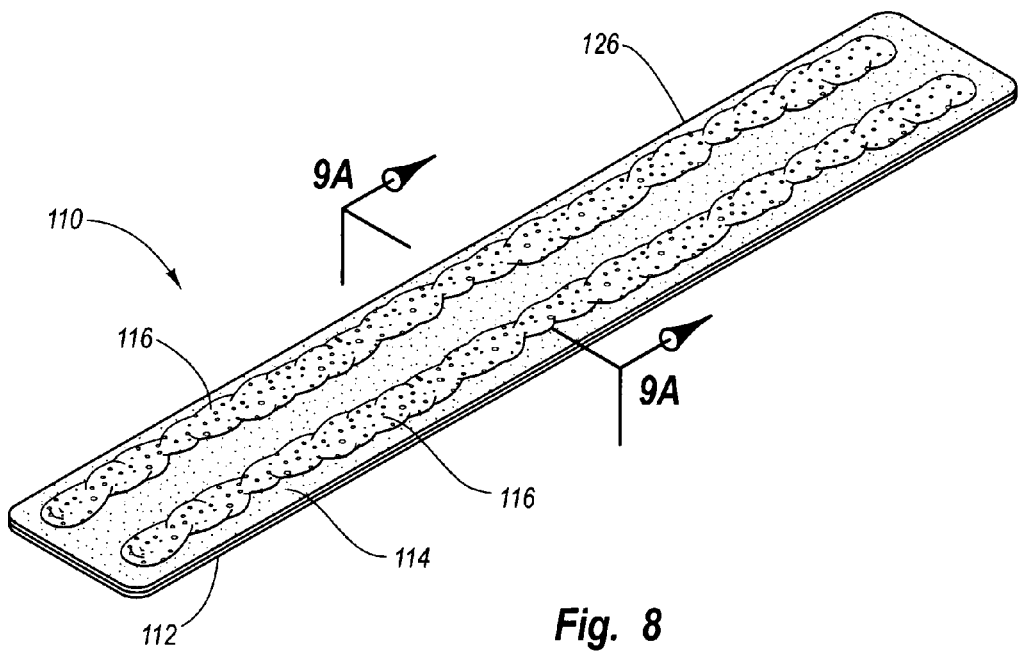
FIG. 8 is a perspective view of an exemplary dental bleaching device according to the invention in the shape of a strip or patch comprising a barrier layer, an adhesive layer, and a dental bleaching gel.

Alternative embodiments of dental bleaching compositions and devices in the form of a strip or patch are depicted in FIGS. 8–11. FIG. 8 is a perspective view of a bleaching strip or patch 110 comprising a barrier layer 112, which preferably comprises a moisture-resistant material, an adhesive layer 114, which preferably comprises a substantially solid adhesive composition, and a dental bleaching gel 116. As best seen in FIG. 9A, the adhesive layer 114 includes an outer surface 120, which is adjacent to an inner surface 122 of the barrier layer 112, and an inner surface 124, which is adjacent to the bleaching gel 116. It is within the scope of the invention for the bleaching gel 116 to directly contact the adhesive layer 114, the barrier layer 112, or both depending on where the bleaching gel 116 is located relative to the adhesive layer 114. In one embodiment, both the bleaching gel 116 and at least a portion of the inner surface 124 of the adhesive layer 114 are designed to directly contact a person's teeth when the bleaching strip 110 is in use. An upper edge 126 of the bleaching strip 110 can be designed so as to terminate at or shy of the gingival margin of a person's dental arch when in use.

Figure 9A:
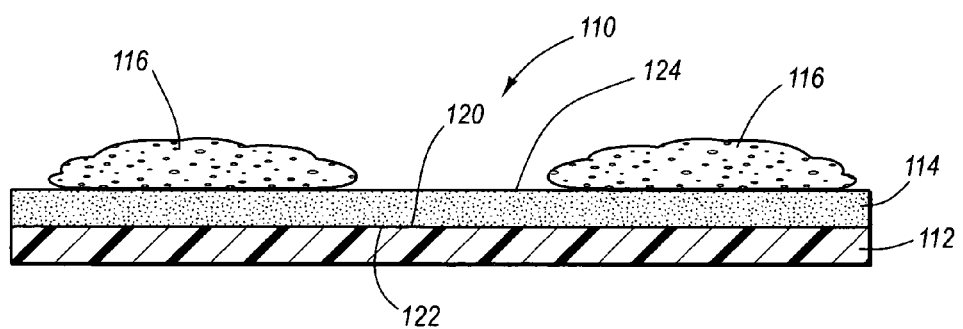
FIG. 9A is a cross-sectional view of the dental bleaching device depicted in FIG. 8.
Figure 9B:
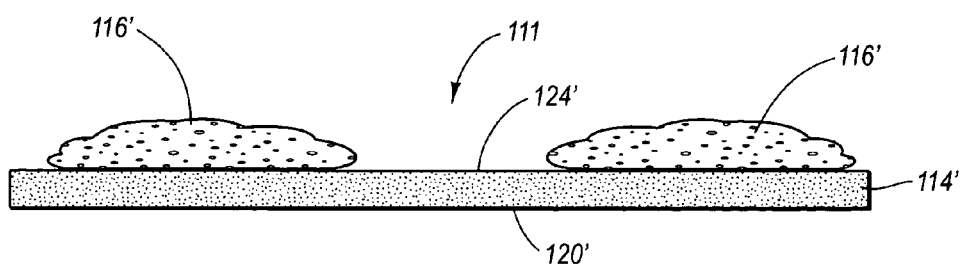
FIG. 9B is a cross-sectional view of an exemplary dental bleaching composition according to the invention in the shape of a strip or patch, but without a barrier layer.

FIG. 9B alternatively depicts a bleaching composition 111 comprising an adhesive layer 114' in the shape of a strip or patch, so as to have an outer surface 120' and an inner surface 124', and bleaching gel 116' adjacent to the inner surface 124' of the adhesive layer 114'. The bleaching composition 111 differs from the bleaching strip 110 of FIGS. 8 and 9A in that it includes no barrier layer. Of course, the outer surface 120' of the adhesive layer 114' may optionally be coated with a water-resistant barrier layer or material if desired (see FIG. 9A) to protect the bleaching composition 111 (more particularly the adhesive layer 114' and bleaching gel 116') from saliva or ambient moisture. The bleaching composition 111 may be sold alone or together with a moisture-resistant barrier layer, or a material used to make a barrier layer, that can be placed adjacent to the outer surface 120' of the adhesive layer 114' prior to or during use.

Figure 9C:
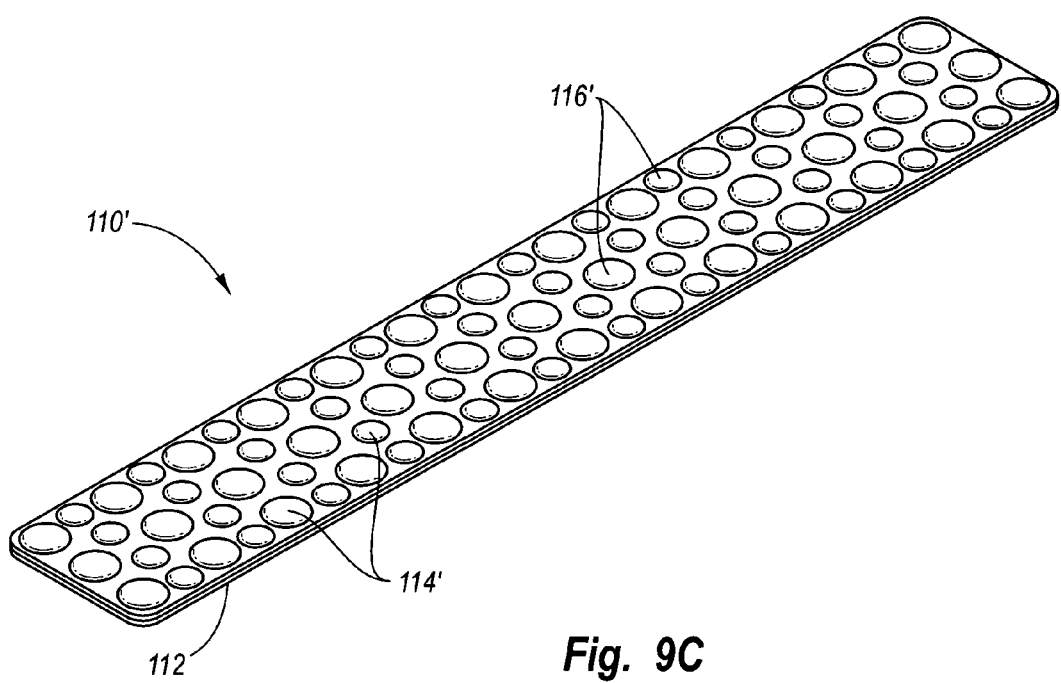
FIG. 9C is a perspective view of an exemplary bleaching device according to the invention that includes a barrier layer and multiple spots or regions of adhesive composition interspersed with multiple spots or regions of bleaching gel.

FIG. 9C alternatively depicts a dental bleaching device 110' that includes a barrier layer 112, regions or spots of an adhesive composition 114' interspersed with regions or spots of a dental bleaching gel 116'. Both the adhesive composition 114' and dental bleaching gel 116' are located adjacent to the barrier layer. In this way, the adhesive composition 114' and dental bleaching gel 116' do not initially touch prior to use, thereby preventing or inhibiting contact between the bleaching agent activator within the adhesive composition 114' and the bleaching agent within the bleaching gel 116' prior to use.

Figure 10:
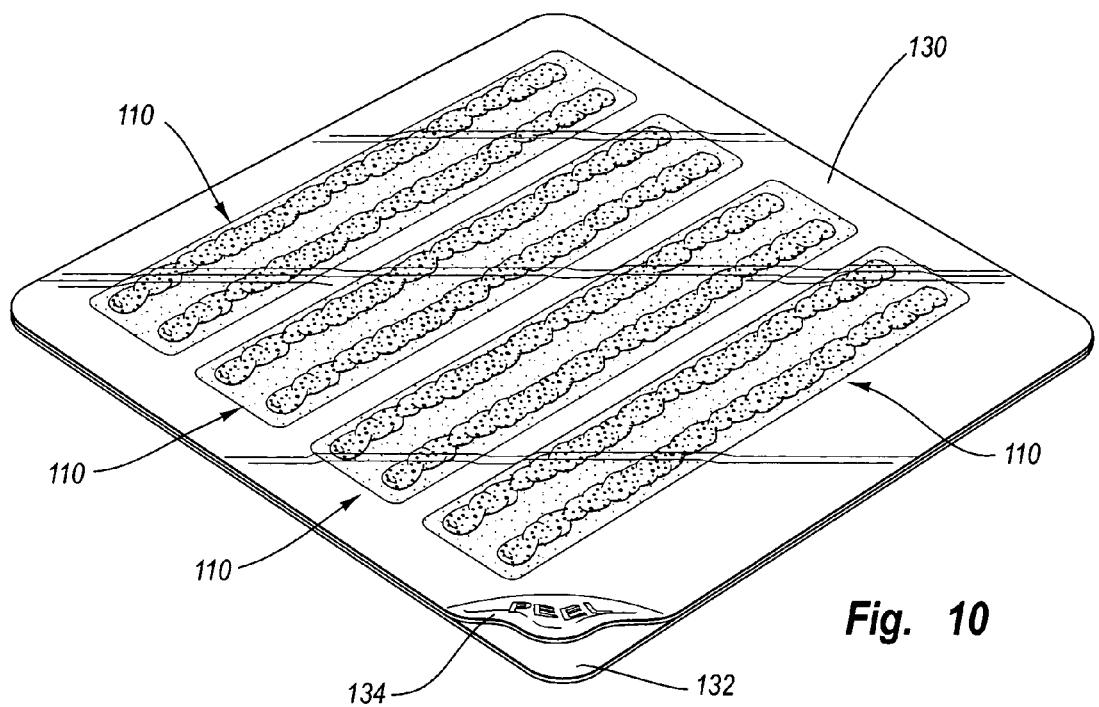
FIG. 10 illustrates multiple bleaching strips (or compositions) according to the a invention contained within a sealed, protective package having a peelable cover.

In order to protect bleaching compositions and devices according to the invention from contaminants during storage and prior to use, they can be packaged within a sealed container or package. As illustrated in FIG. 10, one or more bleaching strips 110 (or bleaching compositions) can be sealed within a protective package 130 that includes a rigid support layer 132 and peelable cover 134. When it desired to use the bleaching strip 110 (or bleaching composition), the peelable cover 134 is removed and the bleaching strip 110 or composition is removed or separated from the support layer 132. In addition to, or instead of, the protective package 130, the bleaching strip 110 or composition may alternatively include a removable protective layer (not shown) that is temporarily placed adjacent to the bleaching gel. When it is desired to use the bleaching strip or composition, the removable protective layer is removed so as to expose the bleaching gel.

Figure 11:
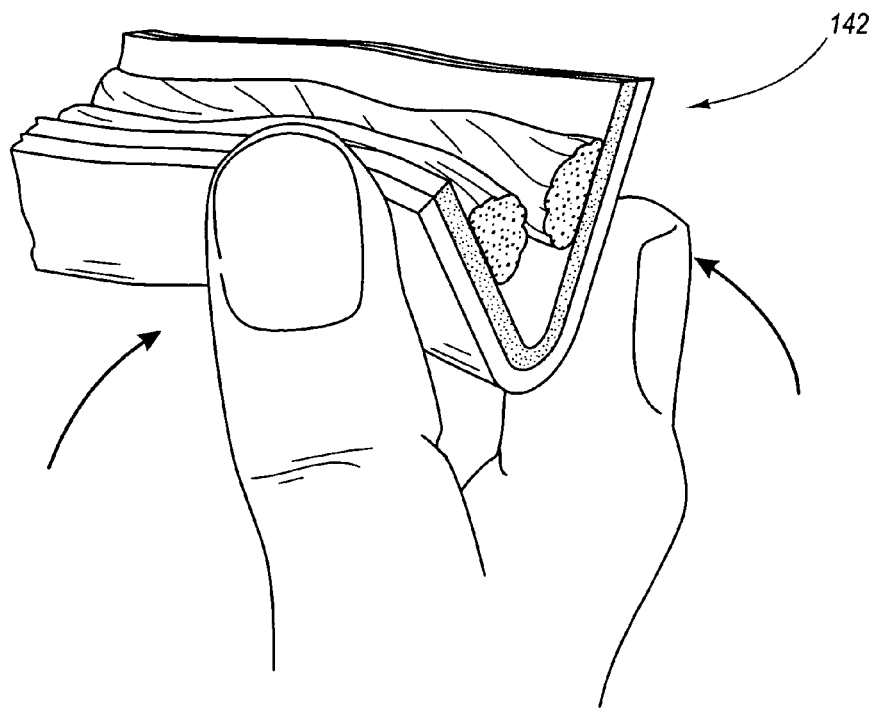
FIG. 11 illustrates a bleaching strip or patch according to the invention being manipulated so as to have an approximate V-shaped cross section prior to placement over a person's teeth.

FIG. 11 shows a bleaching strip 142 being optionally manipulated (such as by bending, curving or folding) so as to have an approximate V-shaped cross section in order to facilitate placement of the bleaching strip 142 over a person's teeth and/or gums.

Notwithstanding the foregoing examples, it will be appreciated that dental bleaching compositions and devices according to the invention can have any profile and longitudinal shape (e.g., they can be flat or have a 3-dimensional shape; they can have a straight or curved longitudinal profile from one end to the other). The front and rear side walls of a tray may define a trough of any desired cross-sectional shape (e.g., the trough can be trapezoidal, rectangular, or any other desired geometric shape).

The size and shape of dental bleaching compositions and devices according to the invention can be tailored to more readily fit either a person's upper dental arch or lower dental arch. They can be sized so as to bleach all or merely a subset of a person's teeth. The dental bleaching compositions and devices may be sufficiently adhesive and flexible so as to readily conform to a wide variety of differently-sized teeth and dental arches. The dental bleaching compositions and devices are advantageously designed so as to substantially cover the front and lingual surfaces of the teeth to bleached. Bleaching both surfaces yields more esthetically appealing teeth, although it is certainly within the scope of the invention to bleach more of one surface than another. Bleaching the front and lingual surfaces helps to bleach the interproximal spaces between a person's teeth. If left unbleached, stained interproximal spaces can form a dark ring or silhouette around each tooth.

In general, the thickness of the barrier layer and/or the adhesive layer can be selected to yield a dental bleaching device having a desired strength and flexibility. In order for the barrier layer to remain flexible so as to conform to a person's teeth, the barrier layer will generally have a thickness ranging from about 0.025 mm to about 1.5 mm, preferably in a range of about 0.05 to about 1 mm. The adhesive layer will generally have a thickness ranging from about 0.1 mm to about 3 mm. The thickness of the adhesive layer can also be selected depending on the intended duration of each bleaching session. In generally, increasing the thickness of the adhesive layer will provide a longer adhesion of the dental bleaching device or composition to a person's teeth. By way of example, for short wear times, the adhesive layer will preferably have a thickness ranging from about 0.1 mm to about 0.5 mm. For intermediate wear times, the adhesive layer will preferably have a thickness ranging from about 0.5 mm to about 2 mm. For professional use and for overnight bleaching, the adhesive layer will preferably have a thickness ranging from about 2 mm to about 3 mm.

The amount of dental bleaching gel can be selected to yield a dental bleaching composition or device having a desired tackiness and/or bleaching potency. In the case where the adhesive layer includes no bleaching agent, the dental bleaching gel will be required to provide the sum total of the bleaching agent. In such cases, the thickness of the dental bleaching gel may be increased, all things being equal. By contrast, in the case where the adhesive layer also includes a bleaching agent, the dental bleaching gel will not be required to provide the entirety of the bleaching agent. In such cases, the thickness of the dental bleaching gel may be decreased, all things being equal.

In addition, the more viscous and tacky the dental bleaching gel, the less deleterious will be the bleaching gel on the overall ability of the bleaching composition or device to adhere to a person's teeth. In such cases, the cross-sectional thickness of the dental bleaching gel may be increased, all things being equal. By contrast, the less viscous and tacky the dental bleaching gel, the less the bleaching gel will tend to adhere to a person's teeth. In such cases, the cross-sectional thickness of the dental bleaching gel may be advantageously decreased, all things being equal.

III. Methods of Making Dental Bleaching Compositions and Bleaching Devices Incorporation Such Compositions The various components that make up the inventive dental bleaching compositions and devices according to the invention can be assembled or brought together in any desired order. According to one embodiment, a shaped adhesive composition or layer is first made by forming a flowable adhesive composition intermediate that is then shaped and dried to form a substantially solid adhesive composition or layer in the form of a dental tray, tray-like device, strip, patch or other desired shape. This may be performed by heating or otherwise causing one or more volatile solvents to be driven off by evaporation, thus leaving behind the substantially solid adhesive layer. Thereafter, a bleaching gel is placed against an inner surface of the adhesive layer and/or the barrier layer. Some or all of the bleaching gel may directly contact the barrier layer to the extent that the adhesive layer has one or more discontinuities or otherwise does not cover the entire barrier layer.

An optional barrier layer may also be placed against an outer surface of the adhesive layer in order to protect the adhesive layer and bleaching gel from ambient moisture within a person's mouth. The barrier layer may be placed against the adhesive layer either before or after the adhesive composition is dried so as to become substantially solidified. In one embodiment, the barrier layer may comprise a pre-formed dental tray. In another, it may comprise a thin, flexible sheet, strip or patch. In yet another embodiment, the barrier layer may initially comprise a flowable barrier material or precursor that is later cured or hardened, such as by removing a solvent by evaporation, by chemical or light curing, or by cooling a thermoplastic melt.

In an alternative embodiment, the adhesive intermediate composition can be cast onto a forming surface and dried to form a substantially solid sheet, which is subsequently molded, stamped, cut or otherwise formed into a desired shape. Thereafter, a dental bleaching gel is attached or applied to an inner surface of the adhesive layer, and a barrier layer is optionally applied or attached to an outer surface of the adhesive layer. The dental bleaching gel can be applied to the adhesive layer before or after the barrier layer, or in the absence of a barrier layer.

According to another embodiment, the adhesive layer can be made by spreading a flowable adhesive composition intermediate onto the surface of a large or continuous polymeric sheet (e.g., using a screeding device). The polymeric sheet and adhesive composition intermediate are then placed into a forced air oven or other appropriate desiccation device in order to heat and drive off a substantial portion of the water or other solvent used to form the flowable adhesive composition intermediate. Removal of the volatile solvent yields an adhesive layer comprising a substantially solid adhesive composition. Thereafter, individual intermediate tray-like devices, patches or strips can be molded, stamped or cut from the large or continuous polymeric sheet coated with the substantially solid adhesive composition or layer and then separated as individual devices. Alternatively, a solid sheet comprising the adhesive composition or layer can be separated from the polymer sheet and molded, stamped, cut or otherwise formed into a desired shape. Once the intermediate devices or adhesive layers have been formed, the dental bleaching gel may be applied or placed adjacent to an inner surface of the adhesive layer.

In yet another embodiment of the invention, a barrier layer in the form of a dental tray, tray-like device (e.g., a customized or non-custom tray), strip, patch or other desired shape can be coated with a flowable adhesive composition intermediate. The adhesive composition intermediate is then heated together with the barrier layer or otherwise allowed to dry in order to form an adhesive layer comprising a substantially solid adhesive composition. Thereafter, a dental bleaching gel is applied to an inner surface of the adhesive layer and/or the barrier layer in order to yield a finished dental bleaching device according to the invention. Any or all of these assembly processes can be performed during commercial manufacture of the bleaching device, or by an end user as part of using a bleaching kit.

IV. Methods of Using Dental Bleaching Compositions and Bleaching Devices Incorporating Such Compositions The dental bleaching compositions and devices according to the invention can be designed to be worn for any desired time period. Increasing the concentration of dental bleaching agent generally reduces the time required to effect bleaching. Nevertheless, due to the extremely comfortable fit and reliable adhesion between the inventive dental bleaching compositions or devices and the person's teeth, it is possible to wear such compositions or devices for extended periods of time in order to ensure more uniform bleaching. They may be designed to be worn while performing normal daily activities, such as talking, eating, drinking, smoking, coughing, smiling, frowning, grimacing, or while sleeping. This greatly decreases their intrusiveness into everyday activities compared to conventional bleaching strips, which do not reliably adhere to teeth, or intrusive bleaching devices such as large, bulky bleaching dental appliances.

The dental bleaching compositions or devices according to the invention may be worn over a person's upper dental arch, lower dental arch, or both simultaneously. The ability to reliably and comfortably wear dental bleaching compositions or devices over the upper and lower dental arches simultaneously is another departure from bleaching strips, which are not recommended for use in bleaching the upper and lower dental arches at the same time.

Figure 12:
FIG. 12 illustrates a person placing a dental bleaching composition or device according to one embodiment of the invention over the upper dental arch.
Figure 13:
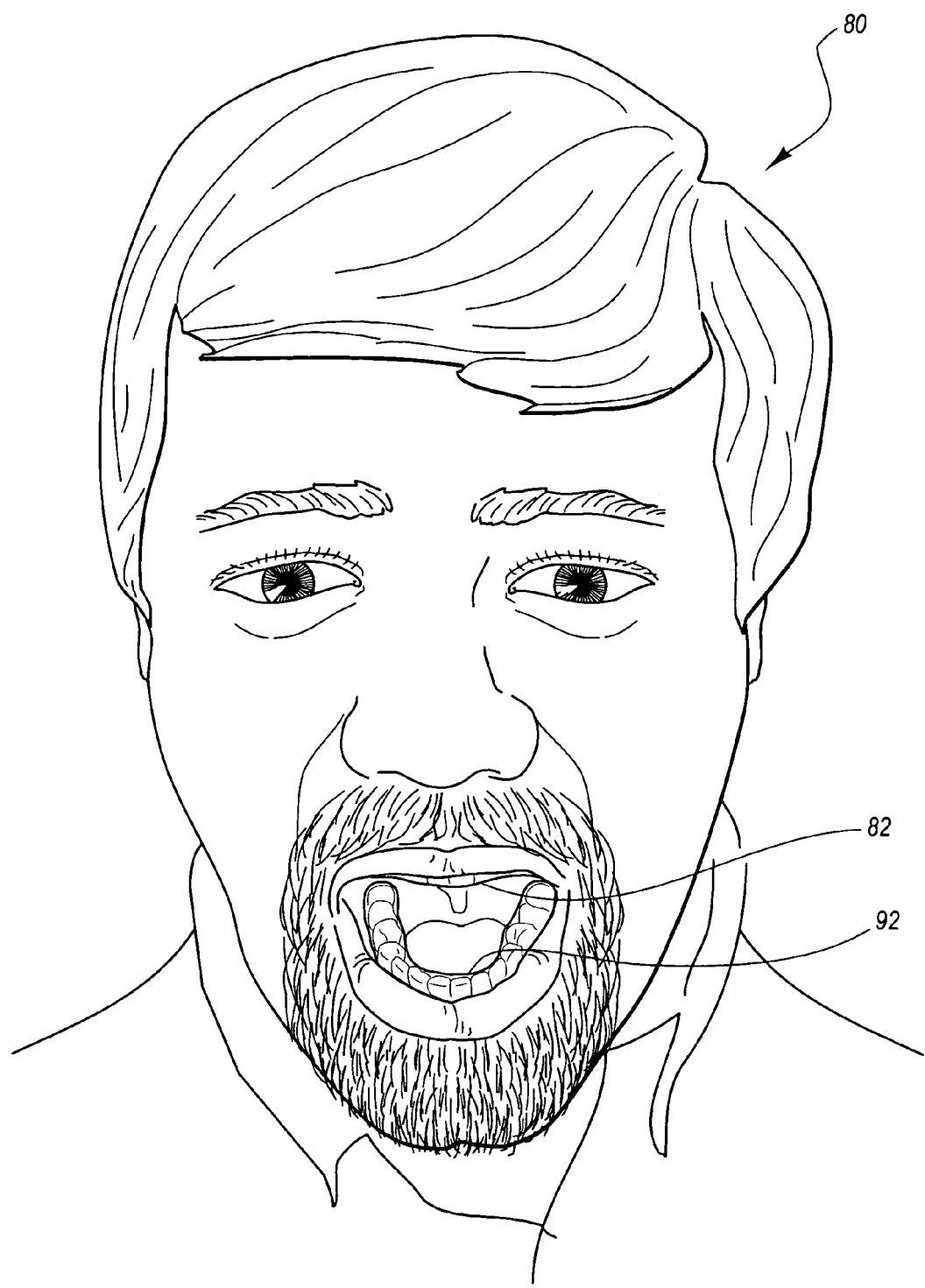
FIG. 13 illustrates a person after placing a dental bleaching composition or device according to one embodiment of the invention over the lower dental arch, with a dental bleaching composition or device already placed over the upper dental arch.

FIG. 12 illustrates a person 80 placing a dental bleaching composition or device 82 over the person's upper dental arch. The dental bleaching composition or device 82 can be in the form of a dental tray, strip, patch or other desired shape. FIG. 13 illustrates the person 80 placing a dental bleaching composition or device 92 over the person's lower dental arch after having placed the dental bleaching composition or device 82 over the upper dental arch. It will be appreciated, however, that the dental bleaching compositions or devices can be placed over a person's upper and lower dental arches in any desired order.

Where the adhesive composition or layer of the bleaching composition or device contains a bleaching agent activator, contacting the bleaching composition or device with saliva or water causes the bleaching agent activator to leach or diffuse out of the adhesive composition, or otherwise become available, so as to react with or otherwise destabilize the bleaching agent within the dental bleaching gel in order to accelerate bleaching. In order to prevent or inhibit premature activation of the dental bleaching agent prior to use, the bleaching may advantageously be initially substantially anhydrous in order to prevent or inhibit diffusion or leaching of the bleaching agent activator from the adhesive composition into the bleaching gel. Alternatively, the bleaching gel may include a stabilizing agent, such as EDTA, in a sufficient quantity to prevent premature activation of the bleaching agent prior to use but not so much as to entire prevent activation during use. In another embodiment, the bleaching agent can occupy discontinuities within the adhesive layer so as to directly contact the barrier layer rather than the adhesive layer, thereby preventing or inhibiting contact between the bleaching gel and adhesive layer prior to use.

To remove the dental bleaching composition or device, a user can pry open a corner of the barrier layer and/or adhesive layer using a fingernail or rigid tool and then pull the remainder off. Any residual adhesive composition and/or bleaching gel that remains adhered to the person's teeth can be removed by washing or flushing water over the person's teeth, and/or by brushing. Although the inventive dental bleaching compositions are very adhesive to teeth when protected from excessive moisture, they can be formulated to quickly break down and dissolve when flushed with excess water and/or by gentle mechanical action (e.g., brushing).

The dental bleaching compositions or devices can be worn for as little as a few minutes or as long as several hours. By way of example, not limitation, a typical bleaching session of fast duration may last from about 10 to about 30 minutes. A bleaching session of intermediate duration may last from about 30 minutes to about 2 hours. A bleaching session of long duration, including professional bleaching or overnight bleaching while a person is sleeping, may last from about 2 hours to about 12 hours.

Bleaching sessions according to the invention may be repeated as many times as needed to obtain a desired degree of tooth bleaching. In some cases, a clinical whitening effect has been observed after only 1–3 whitening sessions. A typical bleaching regimen will preferably include 1–20 bleaching sessions, more preferably 2–15 bleaching sessions, and most preferably 3–10 bleaching sessions.

V. Dental Bleaching Kits

For convenience of use, multiple dental bleaching compositions or devices may be packaged together and sold as a kit. In the case of dental bleaching compositions that do not initially include a barrier layer, a separate barrier layer, or material used to form a barrier layer, may be optionally included within the kit. In one embodiment, the number of dental bleaching compositions or devices provided with each kit may equal the number of sessions that represent a prescribed bleaching regimen. Because of the ease of placing the inventive dental bleaching compositions or devices over a person's teeth, coupled with the reliability with which they adhere to teeth, the likelihood that a particular bleaching compositions or device will fail, or otherwise not work as intended, is greatly diminished compared to conventional bleaching strips.

To efficiently utilize the space within a kit package, multiple dental bleaching compositions or devices can be stacked or interested together. The dental bleaching compositions or devices can be sealed collectively or individually as desired. A protective package 30 is depicted in FIG. 3, and a protective package 130 is depicted in FIG. 10. The bleaching compositions or devices may optionally contain a removable protective layer on an interior surface to protect the bleaching gel from contamination or moisture.

It is within the scope of the invention to provide barrier layers and bleaching composition that are initially separate and that are brought together by the end user. For example, the bleaching composition may comprise a pre-shaped insert in the shape of a horse-shoe that is placed into a trough of a tray-like barrier layer, with or without actually adhering the adhesive layer to the barrier layer. Alternatively, a flowable adhesion composition intermediate can be placed within the trough of a dental tray or tray-like barrier layer and allowed to dry prior to placement of the dental bleaching gel against an inner surface of the substantially solid adhesive layer. Thereafter, a bleaching gel is placed adjacent to an inner surface of the substantially solid adhesive layer. A bleaching gel may also be placed by a user adjacent to an inner surface of a shaped adhesive layer or composition in the absence of a barrier layer, or prior to placing a barrier layer adjacent to an outer surface of the adhesive layer.

VI. Examples of the Preferred Embodiments

The following are several examples of dental bleaching compositions and devices that have been formulated and manufactured according to the invention. The exemplary formulations and manufacturing conditions are given by way of example, and not by limitation, in order to illustrate dental bleaching compositions and devices that have been found to be useful for bleaching a person's teeth. Unless otherwise indicated, all percentages are by weight.

Examples 1–21 are directed to the manufacture of adhesive dental bleaching layers that become more adhesive when moistened by saliva or water. Examples 22–26 are directed to the manufacture of adhesive dental desensitizing layers that become more adhesive when moistened by saliva or water. Examples 27–29 are directed to the manufacture of adhesive medicament layers that become more adhesive when moistened by saliva or water. The adhesive bleaching, desensitizing and medicament layers of Examples 1–29 therefore comprise exemplary adhesive compositions or layers according to the invention. Accordingly, exemplary dental bleaching compositions or devices according to the invention can be manufactured by placing any dental bleaching gel disclosed herein, or known in the art, adjacent to an inner surface of the bleaching, desensitizing, or medicament layers of Examples 1–29.

Examples 30–37 are directed to the manufacture of adhesive compositions or layers that do not include any active agent. Exemplary dental bleaching compositions or devices according to the invention can be manufactured by placing any dental bleaching gel disclosed herein, or known in the art, adjacent to an inner surface of the adhesive layers of Examples 30–37.

Examples 38–43 are directed to exemplary dental bleaching gels that are suitable for use in manufacturing dental bleaching compositions or devices according to the invention. For example, dental bleaching compositions or devices according to the invention can be manufactured by placing the bleaching gels of Examples 38–43 adjacent to any of the adhesive layers described herein, including those formed according to Examples 1–37.

Examples 44–50 describe further variations of exemplary dental bleaching compositions according to the invention.

Example 1

An initially flowable intermediate composition suitable for use in manufacturing a substantially solid, cohesive, and non-flowable dental bleaching layer was formed by mixing together the following components:

| | |
|---|---|
| Carbamide Peroxide | 16% |
| Polyvinyl pyrrolidone (M.W. = 1.3 million) | 38% |
| Water | 46% |

The resulting intermediate composition was spread over the surfaces of three types of flexible polymer sheets: polyethylene sheets having a thickness of approximately 0.15 to 0.18 mm; sheets made of paraffin having a thickness of approximately 0.05 to 0.08 mm; and MYLAR sheets having a thickness of approximately 0.38 mm. The composition was spread using a spatula. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The dried bleaching layer adhered well to each of the polymer sheets. The coated sheets were placed back into the oven overnight to remove additional water.

The coated sheets were removed from the oven a second time, cut apart into smaller-sized pieces, and either used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch.

The strips and tray-like devices were tested by placing them over a person's teeth. The residual saliva present on the tooth surfaces moistened the exposed surface of the bleaching layer and caused it to become sticky and very adhesive to teeth almost immediately. The bleaching devices were pressed against the teeth, which caused them to conform to the natural irregularities of the dental arch and adhere firmly against the teeth. This demonstrated that the bleaching layer formed in this example comprises an excellent adhesive layer.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching gel is not heated prior to placing the dental bleaching device over a person's teeth, which helps preserves the potency and concentration of the dental bleaching agent within the bleaching gel compared to the carbamide peroxide contained within the adhesive bleaching layer.

The dental bleaching devices are worn for varying time periods ranging from several minutes to several hours without becoming dislodged. The formation of oxygen bubbles within the bleaching gel indicates that the bleaching agent remains active. In some cases a noticeable bleaching effect is detected after just one bleaching session (e.g., a 2-hour bleaching session). Noticeable bleaching is typically detected after 1–3 bleaching sessions.

Example 2

An initially flowable intermediate composition suitable for use in manufacturing a substantially solid, cohesive, and non-flowable dental bleaching layer was formed by mixing together the following components:

| | |
|---|---|
| Carbamide Peroxide | 16% |
| PolyOx WSR 101 (M.W. = 1 million) | 7% |
| Water | 77% |

The resulting intermediate composition was spread over the surface of MYLAR sheets using a spatula. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. Unlike the bleaching layer of Example 1, the bleaching layer of Example 2 did not adhere strongly to the polymer sheets but was easily separated therefrom. The coated sheets were placed back into the oven overnight.

The coated sheets were removed from the oven a second time, cut apart into smaller-sized pieces, and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch.

The bleaching devices were tested by placing them over a person's teeth. The residual saliva present on the tooth surfaces moistened the exposed surface of the bleaching layer and caused it to become sticky and adhesive to teeth within a few seconds. The results of Example 2 indicate that, while polyethylene oxide was a satisfactory teeth adhesion agent, it was less satisfactory in promoting adhesion between a bleaching layer and a polymer sheet.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 3

An initially flowable intermediate composition suitable for use in manufacturing a substantially solid, cohesive, and non-flowable dental bleaching layer was formed by mixing together the following components:

| | |
|---|---|
| Carbamide Peroxide | 16% |
| Carbopol 974P | 5% |
| Aqueous NaOH (50%) | 6% |
| Water | 73% |

The resulting intermediate composition was spread over the surface of MYLAR sheets using a spatula. The coated sheets were heated in a forced air oven heated to a temperature of 50–70° C. for approximately 1 hour. The coated sheets were removed from the oven and inspected. Although the intermediate composition dried sufficiently to form a solid, it shrunk considerably, probably because of the large amount of water that was needed to cause Carbopol to form a gel. Shrinkage of the intermediate composition caused the polymer sheet to become partially shriveled up. Whereas shriveling of the polymer sheet was not desired, using carboxypolymethylene as a tooth adhesion agent resulted in a dried bleaching composition that adhered to a polymer sheet.

Thereafter, the coated sheets were removed from the oven after heating overnight, cut apart into smaller-sized pieces, and used as strips or shaped into tray-like devices suitable for placement over a person's teeth. When placed over a person's teeth it took about 5 seconds for the bleaching layer to become moistened enough to start becoming sticky and adhesive to teeth. The strips and tray-like devices were able to conform to the person's teeth and remain in place after being pressed against the teeth for about 30–60 seconds.

The results of Example 3 indicate that, while Carbopol 974 P is able to adhere to a MYLAR sheet and appears to be a satisfactory tooth adhesion agent once the adhesive bleaching layer is sufficiently moistened, it presents a shrinkage problem that can cause undesirable deformation of thin, flexible polymer sheets. One would expect Carbopol 974 P to work better when used with less flexible sheets and/or preformed dental trays of sufficient rigidity to avoid shriveling or unwanted deformation.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 4

An initially flowable intermediate composition suitable for use in manufacturing a substantially solid, cohesive, and non-flowable dental bleaching layer was formed by mixing together the following components:

| | |
|---|---|
| Polyethylene Oxide (M.W. = 100,000) | 20% |
| Glycerin | 2.5% |
| Sodium Percarbonate | 2.4% |
| Water | 75.1% |

The resulting intermediate composition was spread over the surface of MYLAR sheets as in Example 2. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer of Example 4 did not adhere at all to the MYLAR sheets. This indicates that the lower molecular weight polyethylene oxide of Example 4 was even less adhesive to MYLAR sheets than the higher molecular weight polyethylene oxide of Example 2. Sheets comprising an adhesive bleaching layer could also be formed by spreading the intermediate composition on a solid surface such as glass, drying the composition, and then peeling off the dried adhesive layer.

By comparison, when the intermediate composition of Example 1 was applied to a glass surface and then dried, it adhered so strongly that it could not readily be peeled off the glass surface. Instead, it had to be forcefully chipped or pried off using a razor blade.

The dried bleaching layer of Example 4 did, however, adhere to a person's teeth when moistened, although not as well as the bleaching layers of Examples 1–3. This indicates that the bleaching layer of Example 4 might have commercial application as an adhesive layer in a tray-like dental bleaching device to the extent that problems adhering to the barrier layer are overcome or are not an issue.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 5

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Water | 25% |
| Ethanol | 25% |
| Polyvinyl pyrrolidone (M.W. = 1.3 million) | 38% |
| Glycerin | 73% |

The resulting intermediate composition was spread over the surfaces of polyethylene, paraffin, and MYLAR sheets as described in Example 1. The coated sheets were heated in a forced air oven heated to a temperature of 50–70° C. for approximately 45 minutes. The coated sheets were removed from the oven and inspected. The intermediate composition had dried sufficiently so as to form a solid, coherent bleaching layer on the surface of the polymer sheets. Using a mixture of water and ethanol as the solvent allowed the intermediate composition to dry in less than time than the intermediate compositions of Examples 1–4. The inclusion of glycerin helped the bleaching layer remain more flexible and less brittle after drying. The bleaching layer adhered well to each of the polymer sheets. After initial drying, the coated sheets were placed back into the oven overnight.

The coated sheets were removed from the oven a second time, cut apart into smaller-sized pieces, and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 6

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Water | 21% |
| Ethanol | 21% |
| Kollidon VA 64 (M.W. = 60,000) | 40% |
| Carboxy methyl cellulose | 3% |
| PEG 600 | 5% |

Kollidon VA 64 is a polyvinyl pyrrolidone polymer sold by BASF. The resulting intermediate composition was spread over the surfaces of polyethylene, paraffin, and MYLAR sheets as described in Example 1. The coated sheets were heated in a forced air oven heated to a temperature of 50–70° C. for approximately 45 minutes. The coated sheets were removed from the oven and inspected. The intermediate composition had dried sufficiently so as to form a solid, coherent bleaching layer on the surface of the polymer sheets. The inclusion of polyethylene glycol helped the bleaching layer remain more flexible and less brittle after drying. The bleaching layer adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 7

An initially flowable intermediate composition suitable for use in manufacturing a substantially solid, cohesive, and non-flowable dental bleaching layer was formed by mixing together the following components:

| | |
|---|---|
| Carbamide Peroxide | 11.6% |
| Ethanol | 55.8% |
| Kollidon VA 90 F (M.W. = 1.3 million) | 24.4% |
| Carboxy methyl cellulose | 2.3% |
| PEG 600 | 5.8% |

The resulting intermediate composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The intermediate composition had dried sufficiently so as to form a solid, coherent bleaching layer on the surface of the polymer sheets. Using ethanol as the only solvent allowed the intermediate composition to dry in even less time than the compositions of Examples 5 and 6. The bleaching layer adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 8

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Ethanol | 65% |
| Kollidon VA 90 F (M.W. = 1.3 million) | 20% |
| PEG 600 | 5% |

The resulting intermediate composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 9

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Ethanol | 64% |
| Kollidon VA 90 F (M.W. = 1.3 million) | 25% |
| PEG 600 | 1% |

The resulting intermediate composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 10

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Ethanol | 64% |
| Kollidon VA 90 F (M.W. = 1.3 million) | 23% |
| PEG 600 | 1% |
| Aerosil 200 | 2% |

The resulting intermediate composition was spread over the surfaces of polyethylene, paraffin, and MYLAR sheets as described in Example 1. Aerosil 200 was added as a tackifying agent to promote adhesion of the intermediate composition to the polymer sheets. The coated sheets were heated in a forced air oven heated to a temperature of 50–70° C. for approximately 30 minutes. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 11

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Ethanol | 66.9% |
| Kollidon VA 90 F (M.W. = 1.3 million) | 20% |
| PEG 600 | 0.1% |
| Aerosil 200 | 3% |

The resulting intermediate composition was spread over the surfaces of polyethylene, paraffin, and MYLAR sheets as described in Example 1. The coated sheets were heated in a forced air oven heated to a temperature of 50–70° C. for approximately 30 minutes. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 12

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| PolyOx (M.W. = 1 million) | 7.5% |
| Water | 75.5% |
| Glycerin | 5% |
| Aerosil 200 | 2% |

The resulting intermediate composition was spread over the surface of MYLAR sheets as in Example 2. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer of Example 12 did not adhere well to the MYLAR sheets. It also shrunk somewhat after extended drying. The bleaching layer of Example 12 was able to adhere to a person's teeth when moistened.

A dental bleaching gel is placed within the trough of a tray-like composition formed from a bleaching layer of this example, adjacent to an inner surface of the adhesive bleaching layer, to yield a tray-like dental bleaching composition according to the invention. Alternatively, a bleaching gel is placed adjacent to the adhesive layer of a strip. The dental bleaching device of this example is effective in bleaching teeth.

Example 13

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Kollidon 90 F (M.W. = 1.3 million) | 10% |
| Kollidon 30 (M.W. = 50,000) | 20% |
| Water | 53% |
| Glycerin | 5% |
| Aerosil 200 | 2% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent of bleaching layer on the surface of the polymer sheets. The bleaching layer adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 14

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Kollidon 90 F (M.W. = 1.3 million) | 27% |
| Water | 50% |
| Glycerin | 7% |
| Aerosil 200 | 6% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 15

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Kollidon 90 F (M.W. = 1.3 million) | 28% |
| Water | 50% |
| Glycerin | 7% |
| Aerosil 200 | 5% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 16

An initially flowable intermediate composition suitable for use in manufacturing a substantially solid, cohesive, and non-flowable dental bleaching layer was formed by mixing together the following components:

| | |
|---|---|
| Carbamide Peroxide | 15% |
| Polyvinyl pyrrolidone (M.W. = 1.3 million) | 32% |
| Water | 12.8% |
| Ethanol | 20% |
| Glycerin | 10% |
| Aerosil 200 | 5% |
| Calcium EDTA | 0.2% |
| Sodium Lauryl Sulfate | 5% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 17

An initially flowable intermediate composition suitable for use in manufacturing a substantially solid, cohesive, and non-flowable denial bleaching layer was formed by mixing together the following components:

| | |
|---|---|
| Carbamide Peroxide | 15% |
| Polyvinyl pyrrolidone (M.W. = 1.3 million) | 26% |
| Water | 16.8% |
| Ethanol | 25% |
| Glycerin | 15% |
| Calcium EDTA | 0.2% |
| Sodium Lauryl Ether Sulfate | 2% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 18

An initially flowable intermediate composition suitable for use in manufacturing a substantially solid, cohesive, and non-flowable dental bleaching layer was formed by mixing together the following components:

| | |
|---|---|
| Carbamide Peroxide | 15% |
| Polyvinyl pyrrolidone (M.W. = 1.3 million) | 32% |
| Water | 13.8% |
| Ethanol | 20% |
| Glycerin | 12% |

-continued

| | |
|---|---|
| Aerosil 200 | 5% |
| Calcium EDTA | 0.2% |
| Silwet L-7001 | 2% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 19

An initially flowable intermediate composition suitable for use in manufacturing a substantially solid, cohesive, and non-flowable dental bleaching layer was formed by mixing together the following components:

| | |
|---|---|
| Calcium Peroxide | 20% |
| Carbamide Peroxide | 4% |
| Polyvinyl pyrrolidone (M.W. = 1.3 million) | 20% |
| Water | 11.8% |
| Ethanol | 20% |
| Glycerin | 18% |
| Aerosil 200 | 5% |
| Calcium EDTA | 0.2% |
| Sodium Lauryl Sulfate | 2% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 20

An initially flowable intermediate composition suitable for use in manufacturing a substantially solid, cohesive, and non-flowable dental bleaching layer was formed by mixing together the following components:

| | |
|---|---|
| Carbamide Peroxide | 10% |
| Kollidon 90 (M.W. = 1.3 million) | 18.7% |
| Water | 42.3% |
| Ethanol | 13.3% |
| Glycerin | 12% |
| Aerosil 200 | 3.3% |
| Sodium Lauryl Sulfate | 0.33% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 21

An initially flowable intermediate composition suitable for use in manufacturing a substantially solid, cohesive, and non-flowable dental bleaching layer was formed by mixing together the following components:

| | |
|---|---|
| Carbamide Peroxide | 7.1% |
| Kollidon 90 (M.W. = 1.3 million) | 25% |
| Water | 10.7% |
| Ethanol | 50.7% |

-continued

| | |
|---|---|
| Glycerin | 2.9% |
| Aerosil 200 | 3.6% |

The resulting intermediate composition was spread over the surfaces of polyethylene, paraffin, and MYLAR sheets as described in Example 1. The coated sheets were heated in a forced air oven heated to a temperature of 50–70° C. for approximately 1 hour. The coated sheets were removed from the oven and inspected. The intermediate composition had dried sufficiently so as to form a solid, coherent bleaching layer on the surface of the polymer sheets. The bleaching layer adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch. The tray-like devices and strips adhered almost immediately when placed over a person's teeth.

A dental bleaching gel is placed within the trough of a tray-like device of this example, adjacent to an inner surface of the adhesive bleaching layer, to yield a tray-like dental bleaching device according to the invention. Alternatively, a bleaching gel is placed adjacent to the adhesive layer of a strip. The dental bleaching device of this example is effective in bleaching teeth.

Example 22

An initially flowable intermediate composition suitable for use in manufacturing a substantially solid, cohesive, and non-flowable dental desensitizing layer was formed by mixing together the following components:

| | |
|---|---|
| Sodium Fluoride | 0.25% |
| Polyvinyl pyrrolidone (M.W. = 1.3 million) | 30% |
| Water | 69.75% |

The resulting intermediate composition was spread over the surfaces of three types of flexible polymer sheets: polyethylene sheets having a thickness of approximately 0.15 to 0.18 mm; sheets made of paraffin having a thickness of approximately 0.05 to 0.08 mm; and MYLAR sheets having a thickness of approximately 0.38 mm. The intermediate composition was spread using a screeding device. The coated sheets were heated in a forced air oven heated to a temperature of 50–70° C. for approximately 1 hour. The coated sheets were removed from the oven and inspected. The intermediate composition had dried sufficiently so as to form a solid, coherent desensitizing layer on the surface of the polymer sheets. The dried desensitizing composition adhered well to each of the polymer sheets.

The coated sheets were cut apart into smaller-sized pieces and used as strips or shaped into tray-like devices suitable for placement over a person's teeth. The tray-like devices included front and rear side walls that defined a trough having an approximate U- or V-shaped cross section and were curved in the longitudinal dimension to roughly approximate the curvature of a dental arch.

The tray-like devices and strips were tested by placing them over a person's teeth. The residual saliva present on the tooth surfaces moistened the exposed surface of the desensitizing layer and caused it to become sticky and very adhesive to teeth almost immediately. The tray-like devices and strips were pressed against the teeth, which caused them to conform to the natural irregularities of the dental arch and adhere firmly against the teeth. This demonstrated that the desensitizing layer formed in this example comprises an excellent adhesive layer.

A dental bleaching gel is placed within the trough of a tray-like device of this example, adjacent to an inner surface of the adhesive desensitizing layer, to yield a tray-like dental bleaching device according to the invention. Alternatively, a bleaching gel is placed adjacent to the adhesive layer of a strip. The dental bleaching gel is not heated prior to placing the dental bleaching device over a person's teeth, which helps preserves the potency and concentration of the dental bleaching agent within the bleaching gel.

The tray-like dental bleaching device (or strip) is worn for varying time periods ranging from several minutes to several hours without becoming dislodged. The formation of oxygen bubbles within the bleaching gel indicates that the bleaching agent remains active. In some cases a noticeable bleaching effect is detected after just one bleaching session (e.g., a 2-hour bleaching session). Noticeable bleaching is typically detected after 1–3 bleaching sessions. The desensitizing layer helps reduce tooth sensitivity that may otherwise be caused by the bleaching gel.

Example 23

An initially flowable intermediate composition suitable for use in manufacturing a substantially solid, cohesive, and non-flowable dental desensitizing layer was formed by mixing together the following components:

| | |
|---|---|
| Sodium Citrate | 5% |
| Polyvinyl pyrrolidone (M.W. = 1.3 million) | 20% |
| Water | 75% |

The resulting intermediate composition was manufactured into tray-like devices and strips according to the method described in Example 22. The desensitizing layer adhered well to the barrier layers comprising polymer sheets. The tray-like devices and strips were tested by placing them over a person's teeth. The residual saliva present on the tooth surfaces moistened the exposed surface of the desensitizing layer and caused it to become sticky and very adhesive to teeth almost immediately. The tray-like devices and strips were pressed against the teeth, which caused them to conform to the natural irregularities of the dental arch and adhere firmly against the teeth.

A dental bleaching gel is placed within the trough of a tray-like device of this example, adjacent to an inner surface of the adhesive desensitizing layer, to yield a tray-like dental bleaching device according to the invention. Alternatively, a bleaching gel is placed adjacent to the adhesive layer of a strip. The dental bleaching device of this example is effective in bleaching and desensitizing teeth.

Example 24

An initially flowable intermediate composition suitable for use in manufacturing a substantially solid, cohesive, and non-flowable dental desensitizing layer was formed by mixing together the following components:

| | |
|---|---|
| Potassium Nitrate | 3% |
| Polyvinyl pyrrolidone (M.W. = 1.3 million) | 15% |
| Ethanol | 30% |
| Water | 52% |

The resulting intermediate composition was manufactured into tray-like devices and strips according to the method described in Example 22. The desensitizing layer adhered well to the barrier layers comprising polymer sheets. The tray-like devices and strips were tested by placing them over a person's teeth. The residual saliva present on the tooth surfaces moistened the exposed surface of the desensitizing layer and caused it to become sticky and very adhesive to teeth almost immediately. The tray-like devices and strips were pressed against the teeth, which caused them to conform to the natural irregularities of the dental arch and adhere firmly against the teeth.

A dental bleaching gel is placed within the trough of a tray-like device of this example, adjacent to an inner surface of the adhesive desensitizing layer, to yield a tray-like dental bleaching device according to the invention. Alternatively, a bleaching gel is placed adjacent to the adhesive layer of a strip. The dental bleaching device of this example is effective in bleaching and desensitizing teeth.

Example 25

An initially flowable intermediate composition suitable for use in manufacturing a substantially solid, cohesive, and non-flowable dental desensitizing layer was formed by mixing together the following components:

| | |
|---|---|
| Potassium Nitrate | 0.5% |
| Sodium Fluoride | 0.25% |
| Polyvinyl pyrrolidone (M.W. = 1.3 million) | 32% |
| Ethanol | 30% |
| Water | 37.25% |

The resulting intermediate composition was manufactured into tray-like devices and strips according to the method described in Example 22. The desensitizing layer adhered well to the barrier layers comprising polymer sheets. The tray-like devices and strips were tested by placing them over a person's teeth. The residual saliva present on the tooth surfaces moistened the exposed surface of the desensitizing layer and caused it to become sticky and very adhesive to teeth almost immediately. The tray-like devices and strips were pressed against the teeth, which caused them to conform to the natural irregularities of the dental arch and adhere firmly against the teeth.

A dental bleaching gel is placed within the trough of a tray-like device of this example, adjacent to an inner surface of the adhesive desensitizing layer, to yield a tray-like dental bleaching device according to the invention. Alternatively, a bleaching gel is placed adjacent to the adhesive layer of a strip. The dental bleaching device of this example is effective in bleaching and desensitizing teeth.

Example 26

An initially flowable intermediate composition suitable for use in manufacturing a substantially solid, cohesive, and non-flowable dental desensitizing layer was formed by mixing together the following components:

| | |
|---|---|
| Potassium Nitrate | 0.5% |
| Sodium Fluoride | 0.25% |
| Carbamide Peroxide | 15% |
| Polyvinyl pyrrolidone (M.W. = 1.3 million) | 33% |
| Water | 51.25% |

The resulting intermediate composition was manufactured into tray-like devices and strips according to the method described in Example 22. The desensitizing layer adhered well to the barrier layers comprising polymer sheets. The tray-like devices and strips were tested by placing them over a person's teeth. The residual saliva present on the tooth surfaces moistened the exposed surface of the desensitizing layer and caused it to become sticky and very adhesive to teeth almost immediately. The tray-like devices and strips were pressed against the teeth, which caused them to conform to the natural irregularities of the dental arch and adhere firmly against the teeth.

A dental bleaching gel is placed within the trough of a tray-like device of this example, adjacent to an inner surface of the adhesive desensitizing layer, to yield a tray-like dental bleaching device according to the invention. Alternatively, a bleaching gel is placed adjacent to the adhesive layer of a strip. The dental bleaching device of this example is effective in bleaching and desensitizing teeth.

Example 27

An initially flowable intermediate medicament composition suitable for use in manufacturing a substantially solid, cohesive, and non-flowable dental medicament layer was formed by mixing together the following components:

| | |
|---|---|
| Chlorhexidine Gluconate | 2% |
| Polyvinyl pyrrolidone (M.W. = 1.3 million) | 30% |
| Ethanol | 33% |
| Water | 35% |

The resulting intermediate medicament composition was manufactured into tray-like devices and strips according to the method described in Examples 1 or 22. The medicament layer adhered well to the barrier layers comprising polymer sheets. The tray-like devices and strips were tested by placing them over a person's teeth. The residual saliva present on the tooth surfaces moistened the exposed surface of the medicament layer and caused it to become sticky and very adhesive to teeth almost immediately. The tray-like devices and strips were pressed against the teeth, which caused them to conform to the natural irregularities of the dental arch and adhere firmly against the teeth.

A dental bleaching gel is placed within the trough of a tray-like device of this example, adjacent to an inner surface of the adhesive medicament layer, to yield a tray-like dental bleaching device according to the invention. Alternatively, a bleaching gel is placed adjacent to the adhesive layer of a strip. The dental bleaching device of this example is effective in bleaching teeth and delivering an antimicrobial agent.

Example 28

An initially flowable intermediate medicament composition suitable for use in manufacturing a substantially solid, cohesive, and non-flowable dental medicament layer was formed by mixing together the following components:

| | |
|---|---|
| Cetylpyridinium Chloride | 2% |
| Ethanol | 28% |
| Polyvinyl pyrrolidone (M.W. = 1.3 million) | 35% |
| Water | 35% |

The resulting intermediate medicament composition was manufactured into tray-like devices and strips according to the method described in Examples 1 or 22. The medicament layer adhered well to the barrier layers comprising polymer sheets. The tray-like devices and strips were tested by placing them over a person's teeth. The residual saliva present on the tooth surfaces moistened the exposed surface of the medicament layer and caused it to become sticky and very adhesive to teeth almost immediately. The tray-like devices and strips were pressed against the teeth, which caused them to conform to the natural irregularities of the dental arch and adhere firmly against the teeth.

A dental bleaching gel is placed within the trough of a tray-like device of this example, adjacent to an inner surface of the adhesive medicament layer, to yield a tray-like dental bleaching device according to the invention. Alternatively, a bleaching gel is placed adjacent to the adhesive layer of a strip. The dental bleaching device of this example is effective in bleaching teeth and delivering an antimicrobial agent.

Example 29

An initially flowable intermediate medicament composition suitable for use in manufacturing a substantially solid, cohesive, and non-flowable dental medicament layer was formed by mixing together the following components:

| | |
|---|---|
| Phenol | 3% |
| Polyvinyl pyrrolidone (M.W. = 1.3 million) | 35% |
| Ethanol | 62% |

The resulting intermediate medicament composition was manufactured into tray-like devices and strips according to the method described in Examples 1 or 22. The medicament layer adhered well to the barrier layers comprising polymer sheets. The tray-like devices and strips were tested by placing them over a person's teeth. The residual saliva present on the tooth surfaces moistened the exposed surface of the medicament layer and caused it to become sticky and very adhesive to teeth almost immediately. The tray-like devices and strips were pressed against the teeth, which caused them to conform to the natural irregularities of the dental arch and adhere firmly against the teeth.

A dental bleaching gel is placed within the trough of a tray-like device of this example, adjacent to an inner surface of the adhesive medicament layer, to yield a tray-like dental bleaching device according to the invention. Alternatively, a bleaching gel is placed adjacent to the adhesive layer of a strip. The dental bleaching device of this example is effective in bleaching teeth and delivering an antimicrobial agent.

Example 30

An initially flowable adhesive composition intermediate suitable for use in manufacturing a substantially solid adhesive layer was formed by mixing together the following components:

| | |
|---|---|
| Water | 25% |
| Ethanol | 30% |
| Glycerin | 10% |
| Polyvinyl pyrrolidone (M.W. = 1.3 million) | 30% |
| Aerosil 200 | 5% |

The resulting adhesive composition intermediate was manufactured into tray-like compositions, strips or intermediate devices according to the methods described in Examples 1 or 22. The adhesive layer adhered well to the barrier layers comprising polymer sheets. A dental bleaching gel is placed within the trough of a tray-like composition or intermediate device of this example, adjacent to an inner surface of the adhesive layer, to yield a tray-like dental bleaching device according to the invention. Alternatively, a bleaching gel is placed adjacent to the adhesive layer of a strip. The dental bleaching device of this example adheres well to teeth and is effective in bleaching teeth.

Example 31

An initially flowable adhesive composition intermediate suitable for use in manufacturing a substantially solid adhesive layer was formed by mixing together the following components:

| | |
|---|---|
| Water | 20% |
| Ethanol | 30% |
| Glycerin | 15% |
| Polyvinyl pyrrolidone (M.W. = 1.3 million) | 30% |
| Aerosil 200 | 5% |

The resulting adhesive composition intermediate was manufactured into tray-like compositions, strips or intermediate devices according to the methods described in Examples 1 or 22. The adhesive layer adhered well to the barrier layers comprising polymer sheets. A dental bleaching gel is placed within the trough of a tray-like composition or intermediate device of this example, adjacent to an inner surface of the adhesive layer, to yield a tray-like dental bleaching device according to the invention. Alternatively, a bleaching gel is placed adjacent to the adhesive layer of a strip. The dental bleaching device of this example adheres well to teeth and is effective in bleaching teeth.

Example 32

An initially flowable adhesive composition intermediate suitable for use in manufacturing a substantially solid adhesive layer was formed by mixing together the following components:

| | |
|---|---|
| Water | 20% |
| Ethanol | 40% |
| Glycerin | 10% |
| Polyvinyl pyrrolidone (M.W. = 1.3 million) | 30% |

The resulting adhesive composition intermediate was manufactured into tray-like compositions, strips or intermediate devices according to the methods described in Examples 1 or 22. The adhesive layer adhered well to the barrier layers comprising polymer sheets. A dental bleaching gel is placed within the trough of a tray-like composition or intermediate device of this example, adjacent to an inner surface of the adhesive layer, to yield a tray-like dental bleaching device according to the invention. Alternatively, a bleaching gel is placed adjacent to the adhesive layer of a strip. The dental bleaching device of this example adheres well to teeth and is effective in bleaching teeth.

Example 33

An initially flowable adhesive composition intermediate suitable for use in manufacturing a substantially solid adhesive layer was formed by mixing together the following components:

| | |
|---|---|
| Ethanol | 60.6% |
| Glycerin | 5.1% |
| Polyvinyl pyrrolidone (M.W. = 1.3 million) | 30% |
| Aerosil 200 | 4.3% |

The resulting adhesive composition intermediate was manufactured into tray-like compositions, strips or intermediate devices according to the methods described in Examples 1 or 22. The adhesive layer adhered well to the barrier layers comprising polymer sheets. A dental bleaching gel is placed within the trough of a tray-like composition or intermediate device of this example, adjacent to an inner surface of the adhesive layer, to yield a tray-like dental bleaching device according to the invention. Alternatively, a bleaching gel is placed adjacent to the adhesive layer of a strip. The dental bleaching device of this example adheres well to teeth and is effective in bleaching teeth.

Example 34

An initially flowable adhesive composition intermediate suitable for use in manufacturing a substantially solid adhesive layer was formed by mixing together the following components:

| | |
|---|---|
| Ethanol | 61.9% |
| Glycerin | 9.5% |
| Polyvinyl pyrrolidone (M.W. = 1.3 million) | 23.8% |
| Aerosil 200 | 4.8% |

The resulting adhesive composition intermediate was manufactured into tray-like compositions, strips or intermediate devices according to the methods described in Examples 1 or 22. The adhesive layer adhered well to the barrier layers comprising polymer sheets. A dental bleaching gel is placed within the trough of a tray-like composition or intermediate device of this example, adjacent to an inner surface of the adhesive layer, to yield a tray-like dental bleaching device according to the invention. Alternatively, a bleaching gel is placed adjacent to the adhesive layer of a strip. The dental bleaching device of this example adheres well to teeth and is effective in bleaching teeth.

Example 35

An initially flowable adhesive composition intermediate suitable for use in manufacturing a substantially solid adhesive layer was formed by mixing together the following components:

| | |
|---|---|
| Ethanol | 63.6% |
| Glycerin | 9.1% |
| Polyvinyl pyrrolidone (M.W. = 1.3 million) | 27.3% |

The resulting adhesive composition intermediate was manufactured into tray-like compositions, strips or intermediate devices according to the methods described in Examples 1 or 22. The adhesive layer adhered well to the barrier layers comprising polymer sheets. A dental bleaching gel is placed within the trough of a tray-like composition or intermediate device of this example, adjacent to an inner surface of the adhesive layer, to yield a tray-like dental bleaching device according to the invention. Alternatively, a bleaching gel is placed adjacent to the adhesive layer of a strip. The dental bleaching device of this example adheres well to teeth and is effective in bleaching teeth.

Example 36

An initially flowable adhesive composition intermediate suitable for use in manufacturing a substantially solid adhesive layer was formed by mixing together the following components:

| | |
|---|---|
| Ethanol | 44% |
| Polyvinyl pyrrolidone (M.W. = 1.3 million) | 34% |
| Glycerin | 14% |
| Sodium Lauryl Sulfate | 3% |
| Sucralose | 1% |
| Artificial Peach Flavor | 4% |

The resulting adhesive composition intermediate was manufactured into tray-like compositions, strips or intermediate devices according to the methods described in Examples 1 or 22. The adhesive layer adhered well to the barrier layers comprising polymer sheets. A dental bleaching gel is placed adjacent to an inner surface of the adhesive layer to yield a tray-like dental bleaching device according to the invention. Alternatively, a bleaching gel is placed adjacent to the adhesive layer of a strip. The dental bleaching device of this example adheres well to teeth and is effective in bleaching teeth.

Example 37

An initially flowable adhesive composition intermediate suitable for use in manufacturing a substantially solid adhesive layer was formed by mixing together the following components:

| | |
|---|---|
| Ethanol | 31.95% |
| Water | 10% |
| Polyvinyl pyrrolidone (M.W. > 1 million) | 27% |
| Polyvinyl pyrrolidone (M.W. ≈ 60,000) | 10% |
| Sodium Lauryl Sulfate | 0.5% |
| Glycerin | 15% |
| Sucralose (25% solution) | 0.5% |
| Peach Flavor | 4% |
| Potassium Nitrate | 0.8% |
| Sodium Fluoride | 0.25% |

The resulting adhesive composition intermediate was manufactured into tray-like compositions, strips or intermediate devices according to the methods described in Examples 1 or 22. The adhesive layer adhered well to the barrier layers comprising polymer sheets. A dental bleaching gel is placed adjacent to an inner surface of the adhesive layer to yield a tray-like dental bleaching device according to the invention. Alternatively, a bleaching gel is placed adjacent to the adhesive layer of a strip. The dental bleaching device of this example adheres well to teeth and is effective in bleaching teeth.

Example 38

A dental bleaching gel suitable for use in manufacturing dental bleaching compositions and devices according to the invention was formed by mixing together the following components:

| | |
|---|---|
| Carboxy Methyl Cellulose (sodium salt) | 2% |
| Carbamide Peroxide | 22.5% |
| Glycerin | 28% |
| Water | 16.4% |
| Sodium Saccharine Powder | 2% |
| Sodium EDTA | 0.1% |
| Cabosil M-5 ($SiO_2$) | 7% |
| Peach Flavor | 2% |
| Polyethylene Glycol (M.W. = 20,000) | 20% |

The resulting dental bleaching gel was placed within a flexible, thin-walled dental tray and then placed over a person's teeth. Because the bleaching gel was sticky and viscous it was able to adhere and retain the flexible, thin-walled dental tray reasonably well against the person's teeth for a desired period of time (e.g., 1 hour or more). Like any dental tray filled with a conventional dental bleaching composition, the dental tray of this example was easily dislodged from the person's mouth. Moreover, the bleaching gel was easily expressed out of the dental tray and into the person's oral cavity by normal mouth movements, such as talking, yawning or clenching of teeth.

Thereafter, the dental bleaching gel was used to form dental bleaching devices according to the invention by being placed adjacent to one or more adhesive layers of Examples 30–37. A bleaching device was tested by placing it over a person's teeth. The bleaching device adhered very strongly to the person's teeth such that it could only be dislodged by intentionally pealing it off the person's teeth. The bleaching gel was firmly held between the barrier layer and the person's teeth such that it did not readily spill out of the bleaching device and into the person's oral cavity. One reason for this was the much stronger seal between the adhesive layer and the person's teeth than is possible when using the bleaching gel and the dental tray only. Another reason was that the strong adhesion between the adhesive layer and the person's teeth greatly diminished the freedom of movement of the bleaching device relative to the person's teeth.

Example 39

A dental bleaching gel suitable for use in manufacturing dental bleaching compositions and devices according to the invention was formed by mixing together the following components:

| | |
|---|---|
| Water | 19.2% |
| Edetate Disodium | 0.1% |
| Carbamide Peroxide | 18.5% |
| Xylitol C | 7% |
| Glycerin | 25.4% |
| CARBOPOL 974 | 5.3% |
| NaOH (50% in water) | 4.5% |
| Carboxy Methyl Cellulose | 4% |
| Kollidon 90F | 10% |
| Peach Flavor | 3% |
| Sucralose (25% in water) | 3% |

The resulting dental bleaching gel was extremely thick. The dental bleaching gel was used to form dental bleaching devices according to the invention by being placed adjacent to one or more adhesive layers of Examples 30–37. A bleaching device was tested by placing it over a person's teeth. The bleaching device adhered very strongly to the person's teeth such that it could only be dislodged by intentionally pealing it off the person's teeth. The bleaching gel was firmly held between the barrier layer and the person's teeth such that it did not readily spill out of the bleaching device and into the person's oral cavity.

Example 40

A dental bleaching gel suitable for use in manufacturing dental bleaching compositions and devices according to the invention was formed by mixing together the following components:

| | |
|---|---|
| Water | 18% |
| Edetate Disodium | 0.1% |
| Carbamide Peroxide | 18.5% |
| Sucralose (25% in water) | 3% |
| Glycerin | 41.6% |
| CARBOPOL 974 | 5.3% |
| NaOH (50% in water) | 4.5% |
| Kollidon 90F | 2% |
| Carboxy Methyl Cellulose | 4% |
| Peach Flavor | 3% |

The resulting dental bleaching gel had a very good consistency and was able to be easily loaded into a dental tray and then hold the dental tray against a person's teeth. The dental bleaching gel was used to form dental bleaching devices according to the invention by being placed adjacent to one or more adhesive layers of Examples 30–37. A bleaching device was tested by placing it over a person's teeth. The bleaching device adhered very strongly to the person's teeth such that it could only be dislodged by intentionally pealing it off the person's teeth. The bleaching gel was firmly held between the barrier layer and the person's teeth such that it did not readily spill out of the bleaching device and into the person's oral cavity.

Example 41

A dental bleaching gel suitable for use in manufacturing dental bleaching compositions and devices according to the invention was formed by mixing together the following components:

| | |
|---|---|
| Water | 18% |
| EDTA | 0.1% |
| Carbamide Peroxide | 22% |
| Sucralose (25% in water) | 2% |
| Glycerin | 37.1% |
| CARBOPOL 974 | 5.3% |
| NaOH (50% in water) | 4.5% |
| Kollidon 90F | 2% |
| Carboxy Methyl Cellulose | 5% |
| Peach Flavor | 4% |

The resulting dental bleaching gel had a very good consistency and was able to be easily loaded into a dental tray and then hold the dental tray against a person's teeth. The dental bleaching gel was used to form dental bleaching devices according to the invention by being placed adjacent to one or more adhesive layers of Examples 30–37. A bleaching device was tested by placing it over a person's teeth. The bleaching device adhered very strongly to the person's teeth such that it could only be dislodged by intentionally pealing it off the person's teeth. The bleaching gel was firmly held between the barrier layer and the person's teeth such that it did not readily spill out of the bleaching device and into the person's oral cavity.

Example 42

A dental bleaching gel suitable for use in manufacturing dental bleaching compositions and devices according to the invention was formed by mixing together the following components:

| | |
|---|---|
| Water | 18% |
| EDTA | 0.1% |
| Carbamide Peroxide | 22% |
| Sucralose (25% in water) | 2% |
| Glycerin | 40.1% |
| CARBOPOL 974 | 5.3% |
| NaOH (50% in water) | 4.5% |
| Kollidon 90F | 2% |
| Carboxy Methyl Cellulose | 5% |
| Peppermint Oil | 1% |

The resulting dental bleaching gel had a very good consistency and was able to be easily loaded into a dental tray and then hold the dental tray against a person's teeth. The dental bleaching gel was used to form dental bleaching devices according to the invention by being placed adjacent to one or more adhesive layers of Examples 30–37. A bleaching device was tested by placing it over a person's teeth. The bleaching device adhered very strongly to the person's teeth such that it could only be dislodged by intentionally pealing it off the person's teeth. The bleaching gel was firmly held between the barrier layer and the person's teeth such that it did not readily spill out of the bleaching device and into the person's oral cavity.

Example 43

A dental bleaching gel suitable for use in manufacturing dental bleaching compositions and devices according to the invention was formed by mixing together the following components:

| | |
|---|---|
| Water | 22.5% |
| EDTA | 0.1% |
| Carbamide Peroxide | 18.5% |
| Sucralose (25% in water) | 0.75% |
| Glycerin | 41.6% |
| CARBOPOL 974 | 5.3% |
| NaOH (50% in water) | 2.25% |
| Polyvinyl Pyrrolidone (M.W. > 1 million) | 2% |
| Carboxy Methyl Cellulose | 4% |
| Flavor (peach, watermelon or peppermint) | 3% |

The resulting dental bleaching gel had a very good consistency and was able to be easily loaded into a dental tray and then hold the dental tray against a person's teeth. The dental bleaching gel was used to form dental bleaching devices according to the invention by being placed adjacent to one or more adhesive layers of Examples 30–37. A bleaching device was tested by placing it over a person's teeth. The bleaching device adhered very strongly to the person's teeth such that it could only be dislodged by intentionally pealing it off the person's teeth. The bleaching gel was firmly held between the barrier layer and the person's teeth such that it did not readily spill out of the bleaching device and into the person's oral cavity.

Example 44

Any of the dental bleaching gels of Examples 38–43 is placed adjacent to an inner surface of any of the adhesive layers of Examples 1–29 in order to form dental bleaching compositions and devices according to the invention.

Example 45

Any of the dental bleaching gels of Examples 38–43 are modified by adding one or more of a desensitizing agent, remineralizing agent, antimicrobial agent, antiplaque agent, anti-tartar gent, or other medicament in addition to the bleaching agent to yield a bleaching gel having desired properties.

Example 46

Any of the foregoing compositions or devices are modified by including, adjacent to the adhesive layers, one or more dental bleaching or treatment gels disclosed in one or more of the following U.S. patents: U.S. Pat. Nos. 5,376,006; 5,770,182; 5,785,527; 5,851,512; 5,858,332; 5,985,249; 6,306,370; 6,309,625; 6,312,671; 6,322,774; 6,368,576; 6,387,353; 6,500,408; 6,503,485.

Example 47

Dental bleaching devices are manufactured by placing any of the adhesive compositions or layers according to Examples 1–37 adjacent to a tray, strip or patch comprising a bleaching of ethyl vinyl acetate (80%) and polypropylene (20%) and placing a bleaching gel according to any of Examples 38–43 and 45–46 adjacent to a surface of the adhesive composition or layer opposite the tray, strip or patch.

Example 48

Any of the adhesive compositions or layers according to Examples 1–37 is modified by adding an effective amount of one or more bleaching agent activators as discussed elsewhere in the disclosure (e.g., 5% of a an alkali metal or alkaline earth metal base and/or 1% of a metal, metal compound or organo-metallic enzyme) to yield an adhesive activation composition or layer. Adhesive compositions in the examples above that originally included a bleaching agent are modified by omitting the bleaching agent. The bleaching gel, if placed adjacent to the adhesive composition of this example, is substantially anhydrous and/or contains a stabilizing agent for the bleaching agent. The combination of the adhesive activation composition or layer and bleaching gel comprises a dental bleaching composition according to the invention.

Example 49

A bleaching device is manufactured so as to include the dental bleaching composition of Example 48 and a barrier layer adjacent to the adhesive composition or layer.

Example 50

A bleaching device is manufactured so as to include regions or spots of an adhesive activation composition as set forth in Example 48 interspersed with a bleaching gel according to any of Examples 38–43 and 45–46.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. In a dental treatment system that includes a moisture-resistant barrier layer adapted to be placed upon and worn over a treatment composition used in treating a person's teeth, an article of manufacture comprising:
   a substantial dry adhesive activation composition that is sufficiently solid so that it will substantially maintain either a tray-like or a strip-like configuration so as to be adapted for handling and application to a patient's teeth either with or independent of the barrier layer, and the adhesive activation composition having increased adhesiveness to teeth when moistened by saliva or water and, comprising at least one tooth adhesion agent that at least partially contributes to said increased adhesiveness to teeth and at least one bleaching agent activator; and
   a substantially viscous and tacky dental bleaching gel, adjacent to said adhesive activation composition, comprising at least one dental bleaching agent, at least one tackifying agent, and a liquid or gel carrier.

2. An article of manufacture as defined in claim 1, said adhesive activation composition having a tray-like configuration comprising a least two sidewalls that define a trough within which the dental bleaching gel resides prior to use.

3. An article of manufacture as defined in claim 2, said adhesive activation composition having a horse-shoe configuration so as to approximate the curvature of a person's dental arch.

4. An article of manufacture as defined in claim 2, said adhesive activation composition having a substantially straight longitudinal profile prior to use so that longitudinal curving is required when the article is placed over a person's teeth.

5. An article of manufacture as defined in claim 2, at least a portion of said trough having a cross section that is approximately U-shaped, V-shaped, L-shaped, rectangular, or trapezoidal.

6. An article of manufacture as defined in claim 1, said adhesive activation composition comprising a strip or patch prior to use.

7. An article of manufacture as defined in claim 1, wherein said adhesive activation composition is designed so as to approximately terminate at or near a person's gingival margin during use.

8. An article of manufacture as defined in claim 1, said tooth adhesion agent within said adhesive activation composition comprising at least one of polyvinyl pyrrolidone (PVP), carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

9. An article of manufacture as defined in claim 1, said bleaching agent activator comprising at least one of a base, a metal, a metal compound, or an enzyme.

10. An article of manufacture as defined in claim 1, said bleaching agent activator having a concentration in a range of about 0.01% to about 20% by weight of said adhesive activation composition.

11. An article of manufacture as defined in claim 1, said adhesive activation composition further comprising at least one humectant.

12. An article of manufacture as defined in claim 1, wherein said adhesive activation composition has a cross-sectional thickness in a range of about 0.1 mm to about 0.5 mm.

13. An article of manufacture as defined in claim 1, wherein said adhesive activation composition has a cross-sectional thickness in a range of about 0.5 mm to about 2 mm.

14. An article of manufacture as defined in claim 1, wherein said adhesive activation composition has a cross-sectional thickness in a range of about 2 mm to about 3 mm.

15. An article of manufacture as defined in claim 1, said adhesive activation composition further comprising at least one member selected from the group comprising dental desensitizing agents, remineralizing agent, antimicrobial agents, antiplaque agents, and anti-tartar agents.

16. An article of manufacture as defined in claim 1, said dental bleaching gel being substantially anhydrous prior to use.

17. An article of manufacture as defined in claim 1, said dental bleaching gel further comprising at least one member selected from the group comprising dental desensitizing agents, remineralizing agent, antimicrobial agents, antiplaque agents, and anti-tartar agents.

18. An article of manufacture as defined in claim 1, said dental bleaching agent having a concentration in a range of about 1% to about 60% by weight of said dental bleaching gel.

19. An article of manufacture as defined in claim 1, said dental bleaching agent having a concentration in a range of about 3% to about 40% by weight of said dental bleaching gel.

20. An article of manufacture as defined in claim 1, said dental bleaching agent having a concentration in a range of about 5% to about 30% by weight of said dental bleaching gel.

21. An article of manufacture as defined in claim 1, said tackifying agent comprising at least one of polyvinyl pyrrolidone (PVP), carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

22. An article of manufacture as defined in claim 1, further comprising a barrier layer comprising a moisture-resistant material adjacent to an outer surface of said adhesive activation composition so as to provide a barrier to saliva or moisture during use.

23. An article of manufacture as defined in claim 22, said barrier layer being flexible so that it will readily conform to the shape of a person's teeth when in use.

24. An article of manufacture as defined in claim 22, said barrier layer comprising at least one of wax, metal foil, paraffin, ethylene-vinyl acetate copolymer, ethylene-vinyl alcohol copolymer, polycaprolactone, polyolefin, polyethylene, high density polyethylene, low density polyethylene, ultra-low density polyethylene, polypropylene, polytetrafluoroethylene, polyester, polycarbonate, polyurethane, polyamide, or polyesteramide.

25. An article of manufacture as defined in claim 22, said barrier layer having a cross-sectional thickness in a range of about 0.025 mm to about 1.5 mm.

26. An article of manufacture as defined in claim 22, said barrier layer having a cross-sectional thickness in a range of about 0.05 mm to about 1 mm.

27. An article of manufacture as defined in claim 1, further comprising a sealed package within which said adhesive activation composition and bleaching gel are sealed prior to use.

28. A kit for use in desensitizing a person's teeth comprising a plurality of said articles of manufacture according to claim 1.

29. A kit as defined in claim 28, wherein at least some of said articles of manufacture are stacked and internested together.

30. A kit as defined in claim 28, further comprising a barrier layer, or a material used to make a barrier layer, that is positioned adjacent to an outer surface of the adhesive activation composition just prior to use.

31. A method for bleaching a person's teeth comprising obtaining an article of manufacture according to claim 1 and placing it over at least a portion of the person's teeth for a desired time period.

32. An article of manufacture for use in bleaching a person's teeth, comprising:
    a barrier layer comprising a moisture-resistant material;
    a substantially dry adhesive activation composition that is sufficiently solid so that it will substantially maintain either a tray-like or a strip-like configuratian so as to be adapted for handling and application to a patient's teeth, said adhesive activation composition being disposed adjacent to said barrier layer and having increased adhesiveness to teeth when moistened by saliva or water, said adhesive activation composition comprising at least one tooth adhesion agent that at least partially contributes to said increased adhesiveness to teeth and at least one bleaching agent activator; and
    a substantially viscous and tacky dental bleaching gel, adjacent to at least one of said adhesive activation composition or barrier layer, comprising at least one dental bleaching agent, at least one tackifying agent, and a liquid or gel carrier.

33. An article of manufacture as defined in claim 32, said barrier layer having a tray-like configuration comprising a least two sidewalls that define a trough within which the dental bleaching gel resides prior to use.

34. An article of manufacture as defined in claim 33, at least a portion of said trough having a cross section that is approximately U-shaped, V-shaped, L-shaped, rectangular, or trapezoidal.

35. An article of manufacture as defined in claim 33, said barrier layer being initially horseshoe shaped prior to use so as to at least approximately conform to a person's dental arch with minimal longitudinal shaping.

36. An article of manufacture as defined in claim 33, said barrier layer having a substantially straight longitudinal profile prior to use so that longitudinal curving is required when placed over a person's teeth.

37. An article of manufacture as defined in claim 32, said barrier layer being flexible so as to readily conform to the shape of a person's teeth during use.

38. An article of manufacture as defined in claim 32, said barrier layer comprising at least one of wax, metal foil, paraffin, ethylene-vinyl acetate copolymer, ethylene-vinyl alcohol copolymer, polycaprolactone, polyolefin, polyethylene, high density polyethylene, low density polyethylene, ultra-low density polyethylene, polypropylene, polytetrafluoroethylene, polyester, polycarbonate, polyurethane, polyamide, or polyesteramide.

39. An article of manufacture as defined in claim 32, said barrier layer comprising a customized dental tray.

40. An article of manufacture as defined in claim 32, said barrier layer comprising a thin, flexible membrane having no predefined shape, said adhesive layer having sufficiently rigidity so as to a least partially contribute to maintaining said barrier layer in the shape of a dental tray prior to use.

41. An article of manufacture as defined in claim 32, said tooth adhesion agent within said adhesive activation composition comprising at least one of polyvinyl pyrrolidone (PVP), carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

42. An article of manufacture as defined in claim 32, said bleaching agent activator within said adhesive activation composition comprising at least one of a base, a metal, a metal compound or an enzyme.

43. An article of manufacture as defined in claim 32, said bleaching agent activator within said adhesive activation composition having a concentration in a range of about 0.01% to about 20% by weight of said adhesive activation composition.

44. An article of manufacture as defined in claim 32, said adhesive activation composition further comprising at least one member selected from the group comprising dental desensitizing agents, remineralizing agent, antimicrobial agents, antiplaque agents, and anti-tartar agents.

45. An article of manufacture as defined in claim 32, said dental bleaching gel further comprising at least one member selected from the group comprising dental desensitizing agents, remineralizing agent, antimicrobial agents, antiplaque agents, and anti-tartar agents.

46. An article of manufacture as defined in claim 32, said dental bleaching gel positioned adjacent to said barrier layer rather than said adhesive composition so as to prevent or inhibit contact between the bleaching agent activator and bleaching gel prior to use.

47. A kit for use in bleaching a person's teeth comprising a plurality of articles of manufacture according to claim 32.

48. A method for bleaching a person's teeth comprising obtaining a dental bleaching device comprising the barrier layer, adhesive activation composition, and dental bleaching gel of claim 32 and then placing said dental bleaching device over at least a portion of the person's teeth for a desired time period.

49. A method of manufacturing an article for use in a dental treatment system that includes a moisture-resistant barrier layer adapted to be placed upon and worn over a treatment composition used in bleaching a person's teeth, comprising:

mixing together a tooth adhesion agent, a solvent, and a bleaching agent activator to form an adhesive activation composition intermediate;

removing at least a portion of said solvent from said adhesive activation composition intermediate so as to form a substantially solid adhesive composition having increased adhesiveness to teeth when moistened with saliva or water, and that is substantially dry and sufficiently solid so as to be adapted for handling and application to a patient's teeth either with or independent of the moisture-resistant barrier layer, said tooth adhesion agent at least partially contributing to increased adhesiveness to teeth; and placing a substantially viscous and tacky dental bleaching gel adjacent to the adhesive layer for application to the patient's teeth when the adhesion agent is placed on and worn on the teeth under a moisture-resistant barrier layer.

50. A method as defined in claim 49, further comprising placing or forming a barrier layer adjacent to said adhesive activation composition.

51. A method of manufacturing an article for use in bleaching teeth, comprising;

mixing together a tooth adhesion agent, a solvent, and a bleaching agent activator to form an adhesive activation composition intermediate;

placing the adhesive activation composition intermediate adjacent to a barrier layer;

removing at least a portion of said solvent from said adhesive activation composition intermediate so as to form a substantially solid adhesive composition having increased adhesiveness to teeth when moistened with saliva or water, and that is substantially dry and sufficiently solid so that it will essentially maintain either a strip-like or a tray-like configuration, said tooth adhesion agent at least partially contributing to increased adhesiveness to teeth; and placing a substantially viscous and tacky dental bleaching gel adjacent to the adhesive layer for application to the patient's teeth when the adhesion agent is placed on and worn on the teeth under the moisture-resistant barrier layer.

* * * * *

UNITED STATES PATENT AND TRADEMARK OFFICE
CERTIFICATE OF CORRECTION

PATENT NO. : 6,981,874 B2
APPLICATION NO. : 10/784063
DATED : January 3, 2006
INVENTOR(S) : Peter M. Allred and Dan E. Fischer It is certified that error appears in the above-identified patent and that said Letters Patent is hereby corrected as shown below:

Column 4
Line 4, change "an" to --and--

Column 8
Line 53, before "invention" remove [a]

Column 9
Line 15, before "adhesive" insert --the--

Column 12
Line 18, before "protects" insert --that--

Column 13
Line 23, change "cellulose,.butyl" to --cellulose, butyl--

Column 18
Line 36, change "(addition" to --addition--

Column 19
Line 55, after "bleaching device" change "20" to --10--

Column 22
Line 28, before "desired" insert --is--
Line 63, before "bleached" insert --be--

Column 23
Line 14, change "generally" to --general--

Column 25
Line 43, change "entire" to --entirely--

Column 26
Line 24, change "compositions" to --composition--

UNITED STATES PATENT AND TRADEMARK OFFICE
CERTIFICATE OF CORRECTION

PATENT NO.         : 6,981,874 B2
APPLICATION NO. : 10/784063
DATED                  : January 3, 2006
INVENTOR(S)        : Peter M. Allred and Dan E. Fischer It is certified that error appears in the above-identified patent and that said Letters Patent is hereby corrected as shown below:

Column 31
Line 1, remove [than]

Column 35
Line 67, before "bleaching" remove [of]

Column 42
Line 16, change "preserves" to --preserve--

Column 53
Line 2, before "an" remove [a]

Column 54
Line 45, change "agent" to --agents--
Line 54, change "agent" to --agents--

Column 55
Line 56, change "configuration" to --configuration--

Column 56
Line 5, after "comprising" change "a" to --at--
Line 54, change "agent" to --agents--
Line 64, change "agent" to --agents--

Signed and Sealed this

Fourth Day of March, 2008

JON W. DUDAS
*Director of the United States Patent and Trademark Office*